(12) United States Patent
Ling et al.

(10) Patent No.: US 12,108,942 B2
(45) Date of Patent: Oct. 8, 2024

(54) SAMPLE COLLECTION AND TESTING DEVICE

(71) Applicant: Assure Tech. (Hangzhou) Co., Ltd, Zhejiang (CN)

(72) Inventors: Shi Sheng Ling, Zhejiang (CN); Wen Kun Dong, Zhejiang (CN); Yan Yan Wang, Zhejiang (CN); Zhenguo Luo, Houston, TX (US)

(73) Assignee: Assure Tech. (Hangzhou) Co., Ltd, Zhejiang (CN)

( * ) Notice: Subject to any disclaimer, the term of this patent is extended or adjusted under 35 U.S.C. 154(b) by 861 days.

(21) Appl. No.: 17/281,996

(22) PCT Filed: Oct. 31, 2019

(86) PCT No.: PCT/CN2019/114515
§ 371 (c)(1),
(2) Date: Apr. 1, 2021

(87) PCT Pub. No.: WO2021/027082
PCT Pub. Date: Feb. 18, 2021

(65) Prior Publication Data
US 2021/0330300 A1    Oct. 28, 2021

(30) Foreign Application Priority Data

Aug. 9, 2019   (CN) .......................... 201910731545.2

(51) Int. Cl.
*A61B 10/00* (2006.01)
*A61B 5/157* (2006.01)
(52) U.S. Cl.
CPC .......... *A61B 10/0051* (2013.01); *A61B 5/157* (2013.01); *A61B 10/0064* (2013.01); *A61B 10/007* (2013.01)

(58) Field of Classification Search
CPC . A61B 10/0051; A61B 5/157; A61B 10/0064; A61B 10/007; A61B 5/150022;
(Continued)

(56) References Cited

U.S. PATENT DOCUMENTS 5,268,148 A * 12/1993 Seymour ............ A61B 10/0051
422/547
5,335,673 A *  8/1994 Goldstein .......... A61B 10/0051
600/573
(Continued)

FOREIGN PATENT DOCUMENTS

CN        202693584         1/2013
CN        103776660         5/2014
(Continued)

OTHER PUBLICATIONS

"Office Action of China Counterpart Application" issued on Mar. 25, 2020, with English translation thereof, p. 1-p. 17.
(Continued)

*Primary Examiner* — Sean P Dougherty
(74) *Attorney, Agent, or Firm* — JCIP GLOBAL INC.

(57) ABSTRACT

The present invention relates to a sample collection and testing device for analyzing and testing an analyte in a liquid sample. The sample collection device includes a collection inner cavity and a collection outer cavity. The collection inner cavity is disposed inside the collection outer cavity. The collection inner cavity communicates with the collection outer cavity via through holes at a bottom portion of the collection inner cavity. The collection inner cavity is movable between a first position and a second position relative to the collection outer cavity. When the collection inner cavity is at the first position, the liquid sample is collected into the collection outer cavity. When the collection inner
(Continued)

cavity is at the second position, the liquid sample is discharged out of the collection outer cavity.

16 Claims, 13 Drawing Sheets

(58) Field of Classification Search
CPC ........ A61B 5/150259; A61B 5/150305; A61B 5/150343; A61B 5/150755
See application file for complete search history.

(56) References Cited

U.S. PATENT DOCUMENTS

| | | | |
|---|---|---|---|
| 5,380,289 A * | 1/1995 | Hemstreet | A61B 10/007 600/584 |
| 5,575,778 A * | 11/1996 | Hardt | A61B 5/150389 604/200 |
| 2004/0184954 A1 | 9/2004 | Guo et al. | |
| 2004/0237674 A1 | 12/2004 | Wu et al. | |
| 2009/0259145 A1 * | 10/2009 | Bartfeld | A61B 5/154 600/576 |
| 2016/0054202 A1 * | 2/2016 | Yong | A61B 10/0096 73/864.63 |
| 2016/0243544 A1 | 8/2016 | Hu et al. | |
| 2016/0245729 A1 * | 8/2016 | Yamakawa | B01L 3/021 |
| 2016/0302773 A1 | 10/2016 | Lijian et al. | |
| 2017/0042460 A1 * | 2/2017 | Holmes | A61B 5/150389 |
| 2018/0141043 A1 * | 5/2018 | Malcolmson | C12Q 1/6806 |

FOREIGN PATENT DOCUMENTS

| | | |
|---|---|---|
| CN | 106289894 | 1/2017 |
| CN | 107036848 | 8/2017 |
| CN | 110477958 | 11/2019 |

OTHER PUBLICATIONS

"Office Action of China Counterpart Application" issued on Oct. 12, 2020, with English translation thereof, p. 1-p. 10.
"International Search Report (Form PCT/ISA/210) of PCT/CN2019/114515," mailed on May 12, 2020, with English translation thereof, pp. 1-5.

* cited by examiner

SAMPLE COLLECTION AND TESTING DEVICE

CROSS-REFERENCE TO RELATED APPLICATION

This application is a 371 of international application of PCT application serial no. PCT/CN2019/114515, filed on Oct. 31, 2019, which claims the priority benefit of China application no. 201910731545.2, filed on Aug. 9, 2019. The entirety of each of the above mentioned patent applications is hereby incorporated by reference herein and made a part of this specification.

BACKGROUND

Technical Field

The present invention relates to a sample collection and testing device, in particular to a collection and testing device for collecting a fluid sample and mixing the sample with other reaction liquid before test.

Description of Related Art

The following background art is used to help the reader understand the present invention, and should not be considered as the prior art.

The technology of testing the presence of an analyte in a sample using the principle of an immunological binding reaction has been widely used in various fields. This technology can be used to test analytes in various biological samples (saliva, blood, urine, serum, sweat, etc.) to monitor diseases and human health (early pregnancy, tumors, infectious diseases, drugs, etc.). The fundamental principle of this test technology is based on the properties of specific binding between immune molecules, such as antibodies and antigens, haptens/antibodies, biotin and antibiotin.

In the field of medical diagnosis, it is a relatively common method to collect a test liquid sample with a testing device or a test cup and judge whether the liquid sample contains an analyte. Such a testing device or a test cup generally requires that a sample is collected in a sample container, and a related technician inserts a test reagent strip with a part of the reagent strip immersed in the sample, takes the reagent strip out after a certain time, and reads the test result.

US patent applications US2004/0184954 and US2004/0237674 disclose some devices for collecting saliva and testing whether the saliva contains illegal pharmaceutical ingredients. The two patents provide devices and methods for collecting and testing saliva. In these devices, after a sample is sampled on a collector, the sample in an absorption part on the collector is squeezed into a collection cavity by applying an external force, and then tested. In addition, Chinese patent CN202693584U also discloses a device for collecting and testing a sample. In this patent, liquid is collected from saliva collection cotton into a saliva cylinder by means of squeezing between the saliva cylinder and the saliva collection cotton on a connecting rod, then flows into a test cavity in communication with the saliva cylinder, and is tested.

In actual situations, most of the samples are collected to test illegal drugs or drugs of abuse. When the subjects do not cooperate, or the sample volume of the subjects are too small, for sample, the amount of saliva collected is not much, and sometimes, a lot of analytes in the samples need to be tested at the same time, which requires even much sample volume. Therefore, how to enable the collection and testing device to collect as much sample volume as possible and use the sample volume as much as possible in the test is a problem to be solved.

Furthermore, in some tests, samples need to be treated before test. For example, a buffer solution is added to a sample, so that the sample is diluted to reduce the viscosity, and the sample can be smoothly dialyzed on the test strip. Alternatively, a sample needs to react with certain reagent before test. How the buffer solution can be mixed with the sample smoothly, or how the sample reacts with the reagent in advance, thorough mixing or thorough reaction and convenient operation are all problems to be solved.

SUMMARY

The present invention provides an improved sample collection and testing device, which can realize the functions of sample collection, pretreatment and test, and at the same time can realize the function of collecting as many samples as possible for test.

Specifically, the present invention provides a sample collection and testing device for analyzing and testing an analyte in a liquid sample. The sample collection and testing device includes a collection inner cavity and a collection outer cavity. The collection inner cavity is disposed inside the collection outer cavity. The collection inner cavity communicates with the collection outer cavity via through holes at a bottom portion of the collection inner cavity. The collection inner cavity is movable between a first position and a second position relative to the collection outer cavity. When the collection inner cavity is at the first position, the liquid sample is collected into the collection outer cavity, and when the collection inner cavity is at the second position, the liquid sample is discharged out of the collection outer cavity.

In some preferred embodiments, there is a plurality of through holes at the bottom portion of the collection inner cavity, which are evenly distributed at the bottom portion of the collection inner cavity.

In some preferred embodiments, the collection outer cavity includes a cavity body and a platform at an upper part of the cavity body. The collection inner cavity is disposed inside the cavity body. A limiting snap ring is provided on the platform. The limiting snap ring has a restrictive position and a non-restrictive position on the platform. When the limiting snap ring is at the restrictive position, the limiting snap ring is snapped between the collection outer cavity and the collection inner cavity to prevent movement of the collection inner cavity in the collection outer cavity. When the limiting snap ring is at the non-restrictive position, the limiting snap ring is not snapped between the collection outer cavity and the collection inner cavity, and the collection inner cavity is movable in the collection outer cavity from the first position to the second position.

The movement between the collection inner cavity and the collection outer cavity is limited by the limiting snap ring to separate the collection and test of the sample, which facilitates the test of a sample that needs to be pretreated, and also facilitates a delay test.

In some preferred embodiments, symmetrical tabs are provided on an inner side wall of one end of the limiting snap ring, and a protruding annular outer edge is formed at an opening of the collection inner cavity.

In some preferred embodiments, when the limiting snap ring is at the restrictive position, the tabs of the limiting snap ring are under the protruding annular outer edge of the collection inner cavity, the collection inner cavity is snapped onto the limiting snap ring, and the collection inner cavity is not movable in the collection outer cavity. When the limiting snap ring is at the non-restrictive position, the tabs of the limiting snap ring are far away from the protruding annular outer edge of the collection inner cavity, and the collection inner cavity is movable in the collection outer cavity from the first position to the second position.

In some preferred embodiments, the limiting snap ring is provided with an engaging opening on a side wall between the tabs.

In some preferred embodiments, the platform of the collection outer cavity is provided with a strip protrusion. The engaging opening of the limiting snap ring is sleeved on the strip protrusion, and the engaging opening is be slidable along on the strip protrusion, such that the tabs of the limiting snap ring are disposed at or away from the protruding annular outer edge of the collection inner cavity.

The engaging opening of the limiting snap ring is movable on the strip protrusion of the platform to limit the movement trajectory of the limiting snap ring, and the tabs of the limiting snap ring can effectively leave the annular outer edge at the opening of the collection inner cavity, thereby ensuring that the limiting snap ring accurately unlocks the collection inner cavity, and ensuring that the collection inner cavity can move along the collection outer cavity.

In some preferred embodiments, a reaction pad is further disposed in the collection outer cavity. When the collection inner cavity is at the first position, the liquid sample is collected into the collection outer cavity and then reacts with the reaction pad. In some embodiments, a reagent or a substance used to pre-treat the liquid sample is treated on the reaction pad. When the liquid sample contacts the reaction pad, the liquid sample reacts with the reagent on the reaction pad to achieve pretreatment of the liquid sample.

In some preferred embodiments, the device further includes a sample collector. The sample collector includes an absorption part and a collection rod, and the absorption part is connected to a bottom portion of the collection rod, and a sealing washer is disposed in a middle portion of the collection rod.

In some preferred embodiments, an upper part of the collection rod is provided with external threads. An upper part of the collection inner cavity is provided with internal threads, and the collector is fixed with the collection inner cavity by screwing.

In some preferred embodiments, when the collection inner cavity is at the first position, the sample collector is inserted into the collection inner cavity, the sealing washer on the collection rod is sealed with a side wall of the collection inner cavity, the absorption part is squeezed after contacting the bottom portion of the collection inner cavity, and the liquid sample is squeezed from the absorption part into the collection inner cavity, and then flows into the collection outer cavity along the through holes at the bottom portion of the collection inner cavity. The liquid sample flowing into the collection outer cavity reacts with the reaction pad, and the sample collector is screwed and fixed with the collection inner cavity via the external threads of the collection rod and the internal threads of the collection inner cavity.

In some preferred embodiments, a sealing ring is provided on an outer side wall of the collection inner cavity, and the sealing ring forms a seal with the inner wall of the collection outer cavity. A side wall of the collection outer cavity is provided with an air guide hole. After the liquid sample flows into the collection outer cavity, the air in the collection outer cavity is discharged out from the air guide hole. In some preferred embodiments, when the collection inner cavity is at the first position, the air guide hole is located below the sealing ring, the collection outer cavity is not a sealed cavity, and the collection outer cavity communicates with outside via the air guide hole.

The air guide hole can keep air communication between the collection outer cavity and the outside when the collection inner cavity and the sample collector collect the sample, so that the air pressure of the sample reaction cavity is the same as the atmospheric pressure. At this time, the collection inner cavity is sealed and squeezed by the sample collector, and the air pressure in the collection inner cavity is greater than that in the collection outer cavity, so that the liquid sample in the collection inner cavity can be completely collected into the collection outer cavity. In a specific embodiment, the air guide hole has a relatively smaller diameter, usually between 0.5 and 2 mm.

In some preferred embodiments, an outward pointed cone protrusion is provided on an outer wall of the bottom portion of the collection inner cavity. A channel protruding outward is provided on an outer wall of the bottom portion of the collection outer cavity, and a bottom portion of the channel is provided with an opening, and the channel is sealed by a sealing sheet.

In some preferred embodiments, the sealing sheet is an adhesive sticker or an aluminum foil.

In some preferred embodiments, when the collection inner cavity is at the first position, the channel is sealed by the sealing sheet. When the collection inner cavity moves from the first position to the second position and arrives at the second position, the pointed cone protrusion of the collection inner cavity contacts and punctures the sealing sheet, and the liquid sample in the collection outer cavity flows out through the channel and the opening.

In some embodiments, when the collection inner cavity is at the second position, the pointed cone protrusion of the collection inner cavity is in the channel of the collection outer cavity. In this way, the pointed cone protrusion further squeezes the space of the channel, such that the liquid sample in the channel flows out as much as possible. Further, the pointed cone protrusion penetrates through the opening.

In some preferred embodiments, when the collection inner cavity moves from the first position to the second position and arrives at the second position, the sealing ring on the outer wall of the collection inner cavity moves toward a bottom portion of the collection outer cavity along the inner wall of the collection outer cavity, and the sealing ring first seals the air guide hole on the side wall of the collection outer cavity to form a sealed cavity, and then continues to move away from the air guide hole to reduce a volume of the sealed cavity.

When the collection inner cavity is at the second position, the collection outer cavity needs to transfer the liquid therein out. At this time, the sealed cavity formed after the air guide hole is sealed is conducive to compression and increases the air pressure of the collection outer cavity, thereby quickly transferring the liquid sample as much as possible.

In some preferred embodiments, the sample collection and testing device further includes a cover, and the cover is movably connected to a side wall of the platform of the collection outer cavity. The cover presses and covers the platform of the collection outer cavity to press the sample collector and the collection inner cavity that are fixedly connected, such that the collection inner cavity moves in the collection outer cavity from the first position toward the second position, and after the cover completely covers the platform, the collection inner cavity is at the second position.

In some preferred embodiments, a handle is provided at a top portion of the collection rod. As the cover presses and covers the platform of the collection outer cavity, an inner top portion of the cover contacts and presses the handle, and the handle moves down, thereby driving the collector and the collection inner cavity to move in the collection outer cavity from the first position to the second position.

In some preferred embodiments, the sample collection and testing device further includes an outer cylinder and a test element in the outer cylinder. The collection outer cavity is disposed in the outer cylinder, and the collection outer cavity communicates with the outer cylinder and the test element via the channel and the opening at the bottom portion.

In some preferred embodiments, when the collection inner cavity is at the first position, the collection inner cavity is in liquid communication with the collection outer cavity, and when the collection inner cavity is at the second position, the collection outer cavity is in communication with the outer cylinder and the test element.

In some preferred embodiments, a groove is provided at a bottom portion of the outer cylinder, and the bottom portion of the channel and the opening are disposed in the groove.

In some preferred embodiments, a protruding base is provided at the bottom portion of the outer cylinder, and a fence is provided around the protruding base. The bottom portion of the collection outer cavity is on the protruding base.

In some preferred embodiments, the groove is disposed on the protruding base.

In some preferred embodiments, a test cavity is provided at the bottom portion of the outer cylinder, and the test cavity is in communication with the groove. The test element is disposed in the test cavity.

In some preferred embodiments, there may be one or a plurality of test elements. The plurality of test elements are used to test different analytes in the sample, respectively.

In some preferred embodiments, the cover is provided with a U-shaped buckle, and the side wall of the platform is provided with a protruding block at the corresponding position.

In the present invention, after the sample is collected from the collector into the collection inner cavity and enters the collection outer cavity, in order to ensure enough time for the sample to react with the substance or reagent or reaction pad in the reaction cavity such that the sample can be fully pretreated, the device is usually stood for a certain time, for example, 1 to 5 minutes, 1 minute, 2 minutes, or 3 minutes, etc. Of course, the test may also not be performed immediately after the sample is pretreated in the reaction cavity. Therefore, the device can be stood for a long time before the test, usually more than 1 minute, for example, 1 minute to 1 day.

Beneficial Effects

The device of the present invention can complete the collection, buffer reaction and test of a liquid sample in a one-stop manner, are particularly suitable for the test of a sample that needs to be pretreated for a certain time, and can test the sample within a set time. In addition, the device of the present invention can maximize the collection of a sample, which improves the accuracy of tests and facilitates the test of multiple analytes in the same sample.

DESCRIPTION OF THE EMBODIMENTS

Figure 1:
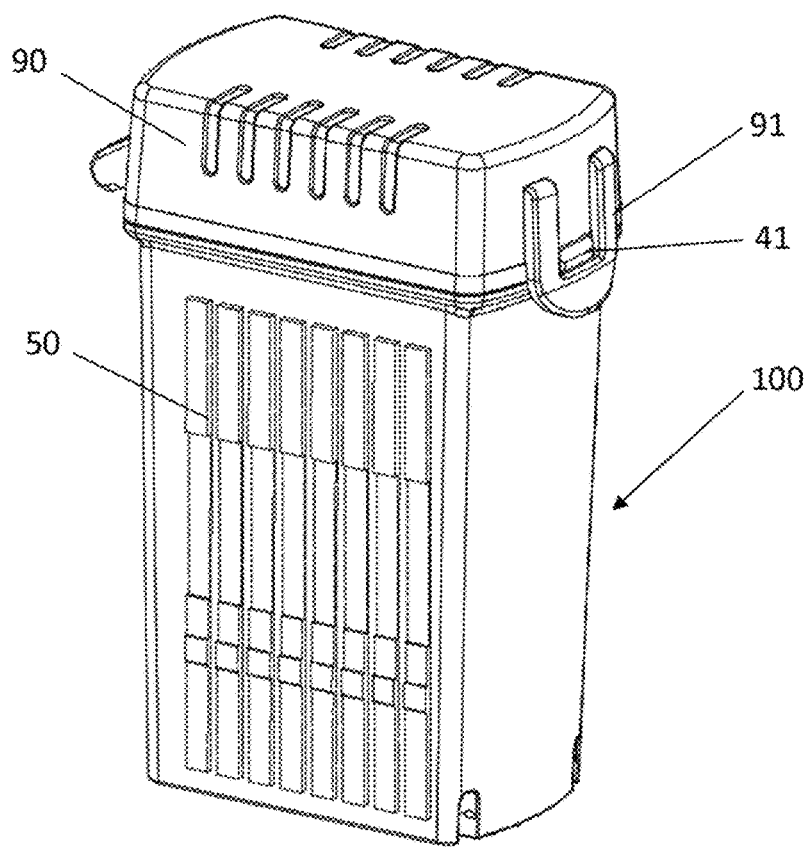
FIG. 1 is an overall schematic diagram of a sample collection and testing device according to the present invention.

The structures or technical terms used in the present invention will be further described below.

Test

Test means to assay or detect the presence of a substance or material, for example, but not limited to, chemicals, organic compounds, inorganic compounds, metabolites, drugs or drug metabolites, organic tissues or metabolites of organic tissues, nucleic acids, proteins or polymers. In addition, the test denotes the amount of the test substance or material. Furthermore, the test also denotes immunoassay, chemical test, enzyme test, etc.

Sample

Samples described in the present invention refer to those substances that can be used to test, assay or diagnose the presence of analytes of interest. The samples may be, for example, liquid samples. The liquid samples may include blood, plasma, serum, urine, saliva and various secretions, and may also include liquid solutions formed after solid samples and semi-solid samples are pretreated. The collected samples can be used for immunoassay, chemical test, enzyme test and other methods to test the presence of analytes. In a preferred embodiment, the samples of the present invention are saliva samples.

Analyte

With the device and method of the present invention, any analyte can be analyzed. Analytes can be tested in any liquid or liquefied samples, such as urine, saliva, blood, plasma, or serum. Analytes may also be haptens, including drugs (such as drugs of abuse). "Drugs of abuse" (DOA) refer to drugs for non-medical purposes (usually paralyzing nerves). The device can also be used to test such drugs that have medical purposes but are easily overdosed, such as tricyclic antidepressants (imipramine or analogues) and acetaminophen. After being absorbed by the human body, these drugs are decomposed into different small molecular substances. These small molecular substances are present in body fluids such as blood, urine, saliva and sweat, or in part of the body fluids.

Test Element 50

The test element 50 may be a transverse flow test strip, which can be used to test a variety of analytes. Of course, other suitable test elements may also be used in the present invention. Various test elements may be combined and used in the present invention. One form is test paper. The test paper used to analyze analytes in samples (such as drugs or metabolites indicating physical conditions) may be in various forms, such as immunoassay or chemical analysis. A non-competitive or competitive analysis mode may be used for the test paper. The test paper includes a water absorbing material having a sample receiving zone, a reagent zone, and a test zone. A sample is added to the sample receiving zone and flows to the reagent zone by capillary action. In the reagent zone, if an analyte is present, the sample is bound to the reagent. The sample then continues to flow to the test zone. Some other reagents, such as molecules specifically bound to the analyte, are immobilized in the test zone. These reagents react with the analyte (if present) in the sample and bind the analyte in the zone, or are bound with one of the reagents in the reagent zone. A marker for displaying a test signal is present in the reagent zone or a separated marker zone.

The typical non-competitive analysis mode is a follows. If the sample contains the analyte, a signal will be generated, and if the sample does not contain the analyte, no signal will be generated. In the competitive method, a signal is generated if the analyte is not present in the sample, and no signal is generated if the analyte is present.

The test element 50 may be test paper made of a material that absorbs water or does not absorb water. The test paper may include a variety of materials for liquid sample delivery. One material of the test paper may cover another material, for example, a filter paper covers a nitrocellulose membrane. One or more materials may be used for one zone of the test paper, and other different one or more materials may be used for another zone. The test paper may be adhered to a support or a hard surface to increase the strength of the test paper held. The analyte is tested by a signal generation system, for example, one signal generation system or a composition of more signal generation systems is immobilized in the analyte test zone of the test paper by using one or more enzymes that specifically react with the analyte, and using the aforementioned method of immobilizing a specific binding substance on a test paper. The substance that generates the signal may be on the sample receiving zone, the reagent zone, or the test zone, or the entire test paper, and the substance can fill one or more materials of the test paper. A signal substance-containing solution is added to the surface of the test paper or one or more materials of the test paper are immersed in the signal substance-containing solution. The test paper added with the signal substance-containing solution is dried.

The zones of the test paper can be arranged in the following manner. A sample receiving zone, a reagent zone, a test zone, a control zone, a zone for determining whether a sample is adulterated, and a liquid sample absorption zone. The control zone is behind the test zone. All the zones can be arranged on a test paper made of only one material. Different materials may also be used for different zones. Each zone may be in direct contact with a liquid sample, or different zones are arranged according to the direction of flow of the liquid sample, and the end of each zone is connected with and overlaps the front end of another zone. The materials used may be the ones with good water absorption, such as a filter paper, glass fibers or a nitrocellulose membrane. The test paper may also be in other forms. In some preferred embodiments, there may be one or more test elements. The more test elements may be used to test different analytes in the sample.

Sample Collector 10

Figure 2:
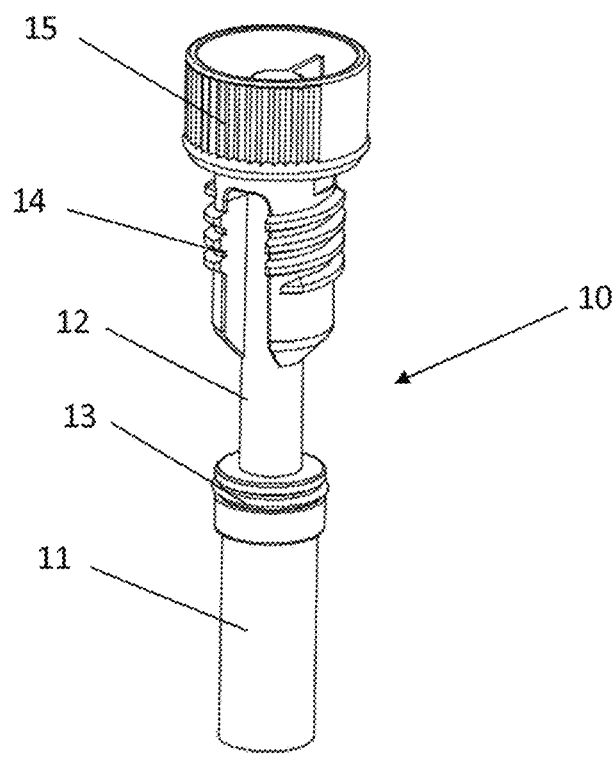
FIG. 2 is a schematic diagram of a collector according to the present invention.
Figure 3:
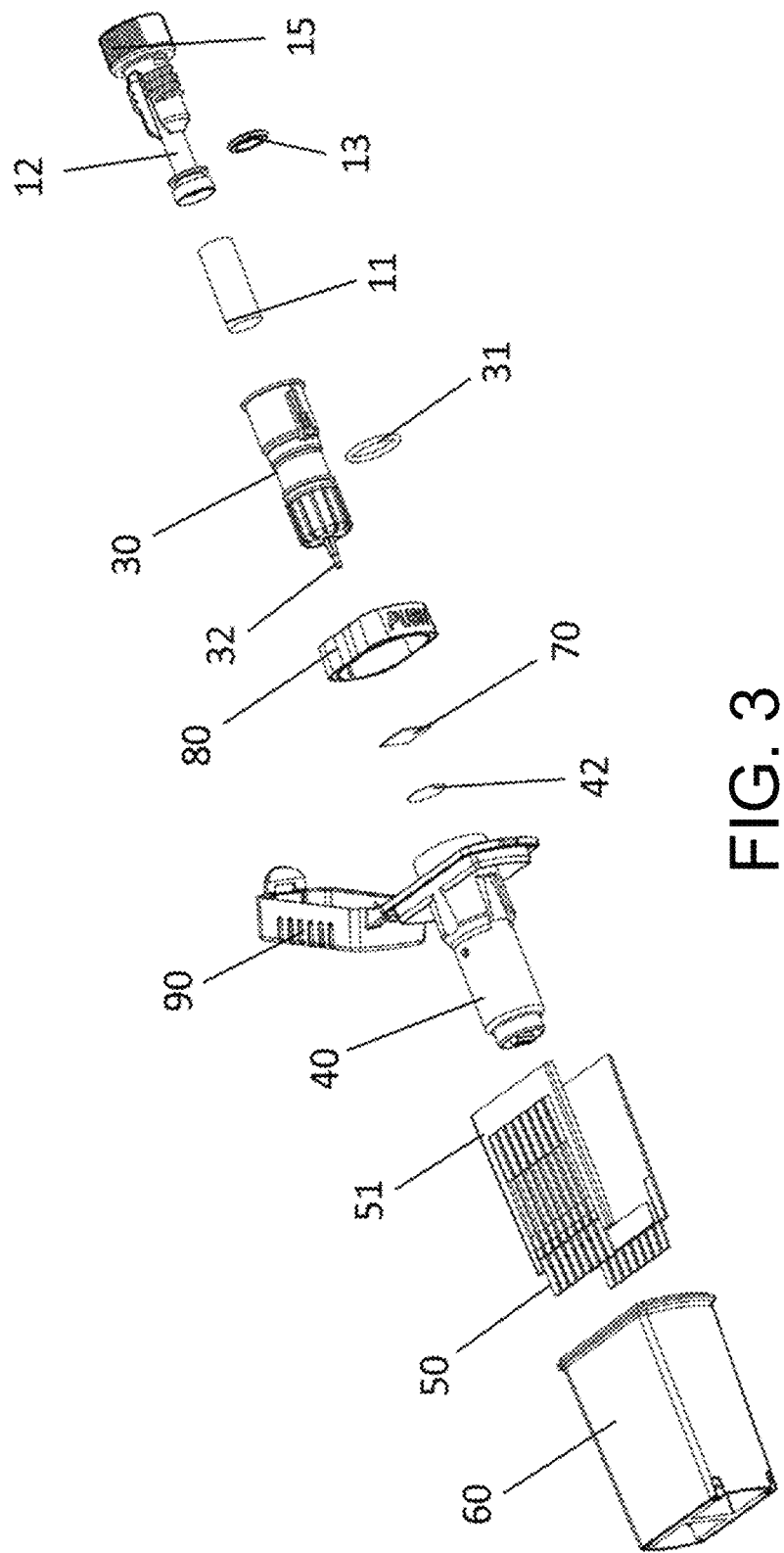
FIG. 3 is an exploded schematic diagram of the sample collection and testing device according to the present invention.
Figure 4:
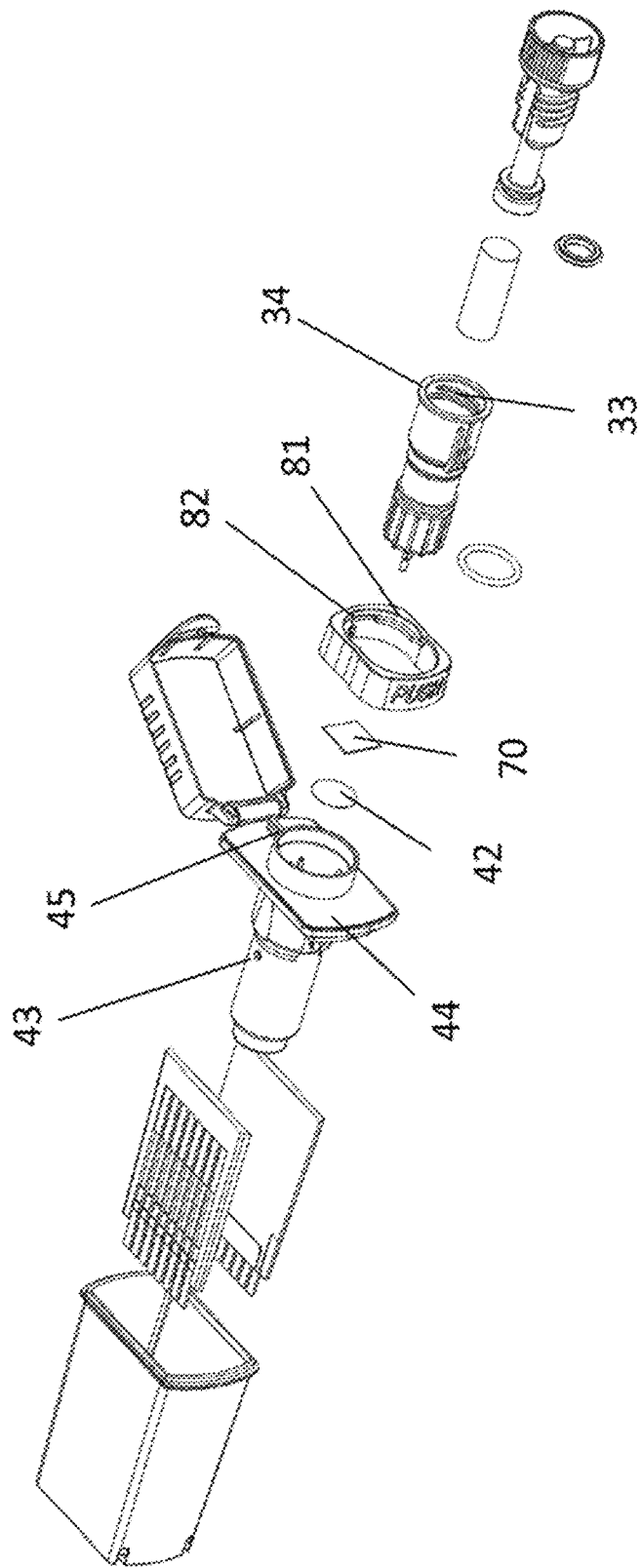
FIG. 4 is another exploded schematic diagram of the sample collection and testing device according to the present invention.

Generally, the sample collector includes an absorption part 11 and a collection rod 12. As shown in FIG. 2, the absorbing member 11 is at one end of the collection rod 12. The absorption part 11 is usually made of medical-grade sponge or foamed plastic commonly used in the art. However, many other materials can also be made into the absorption part, such as cotton or paper, or any other material with water absorption. The collection rod is usually rigid, which facilitates the operation on the absorption part. The collection rod may be made of materials commonly used in the art, such as plastic, wood, metal or cardboard. In some embodiments, an O-shaped sealing washer 13 is provided in a middle portion of the collection rod 12 to seal a collection cavity receiving the collector, so that the liquid sample therein does not flow back to the collection rod 12. In some more preferred ways, in order that the liquid in the absorption part 11 is squeezed more thoroughly and the sample collector 10 is prevented from being placed at random, the sample collector is provided with threads 14 to match and lock with the collection cavity, so that the collector 10 is fixed with the collection cavity. In some embodiments, a handle 15 is provided on a top portion of the collection rod to facilitate an operator to operate the collector 10.

Test Cavity 20

The test cavity 20 is usually a cavity for receiving the test element 50, and a liquid sample can enter the cavity 20 to contact the test element 50 for test. The test cavity is in various shapes, and can be designed according to the shape and number of the test element 50 to be received. In the present invention, the test element is a test strip 50. In some embodiments, a plurality of test strips can be integrated on one test board 51, then the test board 51 is placed in the test cavity 20, and the sample receiving zones of the test strips are at a position of the test cavity in contact with a sample (usually at the bottom portion of the test cavity). In the present invention, the test cavity is in an outer cylinder, and is enclosed by a side wall of the outer cylinder and a protruding base. In some preferred embodiments, the outer cylinder 60 has a window, and the window is opposite to the test zone of the test strip to facilitate the observation of the test result of the test strip. Alternatively, in some other embodiments, the outer cylinder 60 itself is transparent, which facilitates the observation of the test result of the test strip.

In the following detailed description, the reference texts accompanying the legends are a part here, and are described by way of examples to illustrate the specific solutions that may be implemented in the present invention. It is not excluded that the present invention may also be implemented by other specific solutions and the structure of the present invention may be changed without departing from the scope of use of the present invention.

Figure 8:
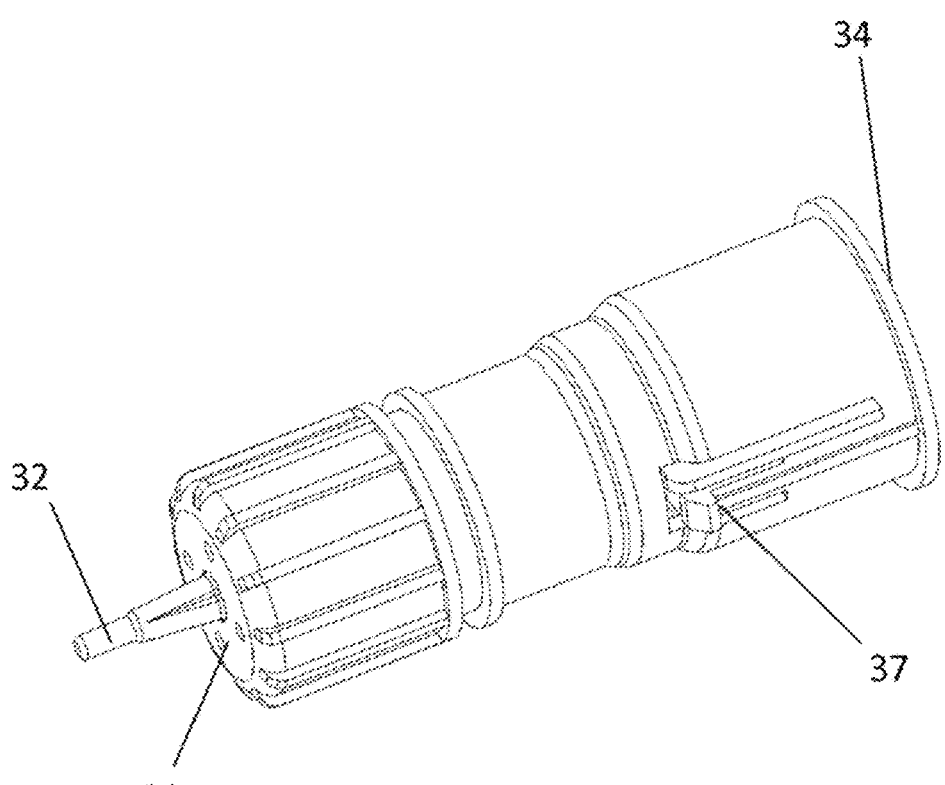
FIG. 8 is a schematic diagram of a collection inner cavity according to the present invention.
Figure 13:
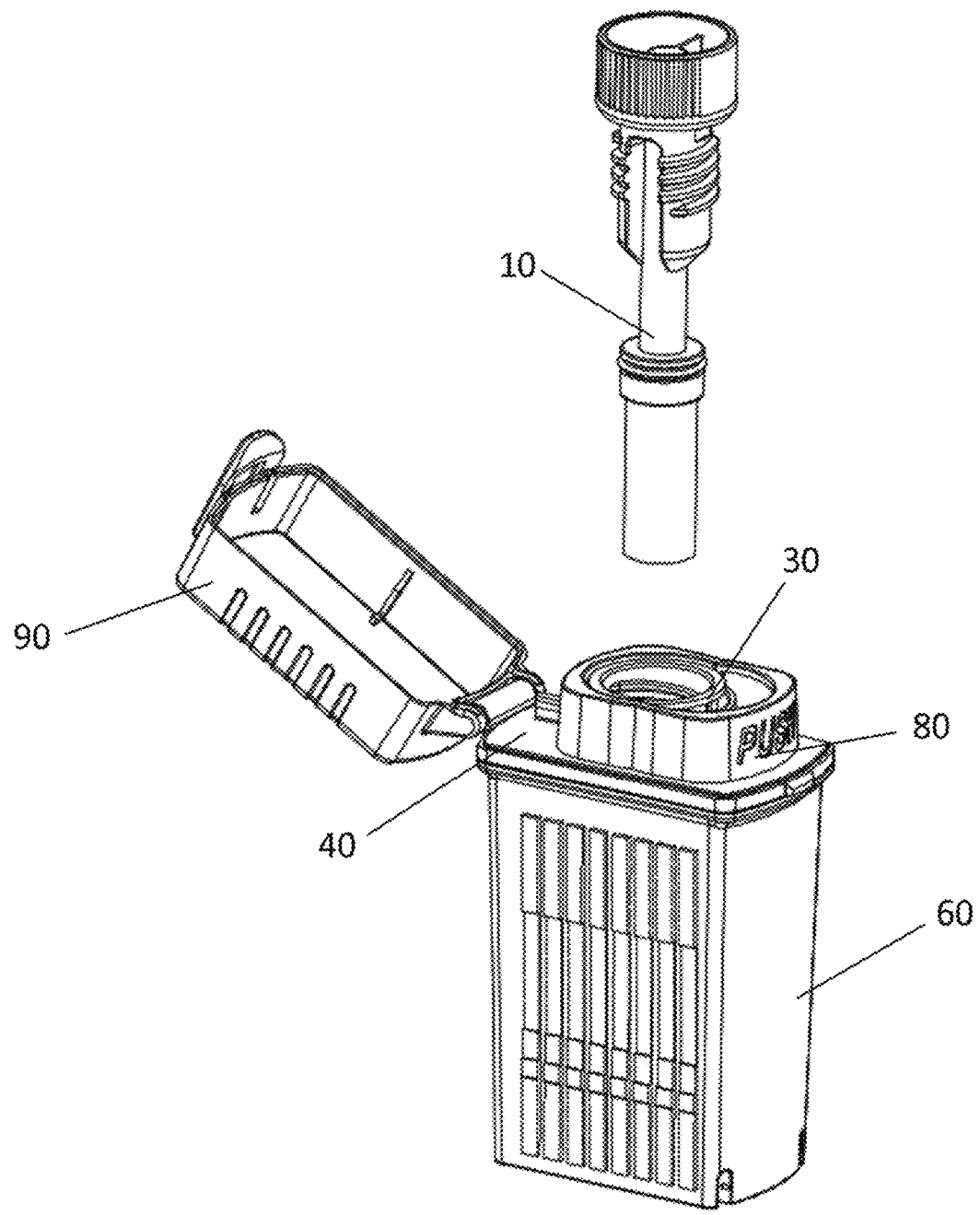
FIG. 13 is a schematic diagram of the sample collection and testing device according to the present invention in an initial state (the collection inner cavity is at a first position and the limiting snap ring is at the restrictive position).
Figure 14:
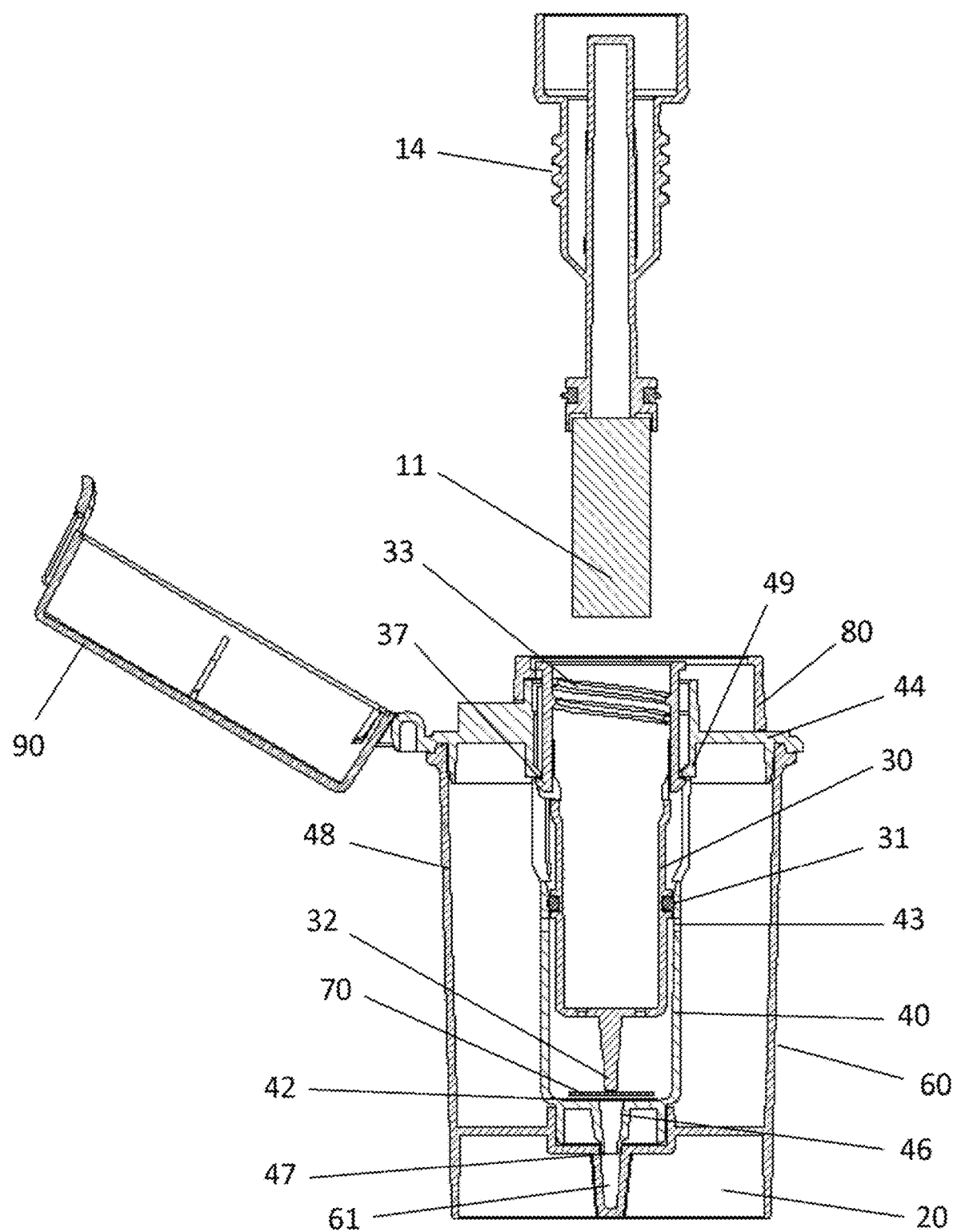
FIG. 14 is a schematic cross-sectional diagram of the sample collection and testing device according to the present invention in the initial state (the collection inner cavity is at the first position and the limiting snap ring is at the restrictive position).
Figure 22:
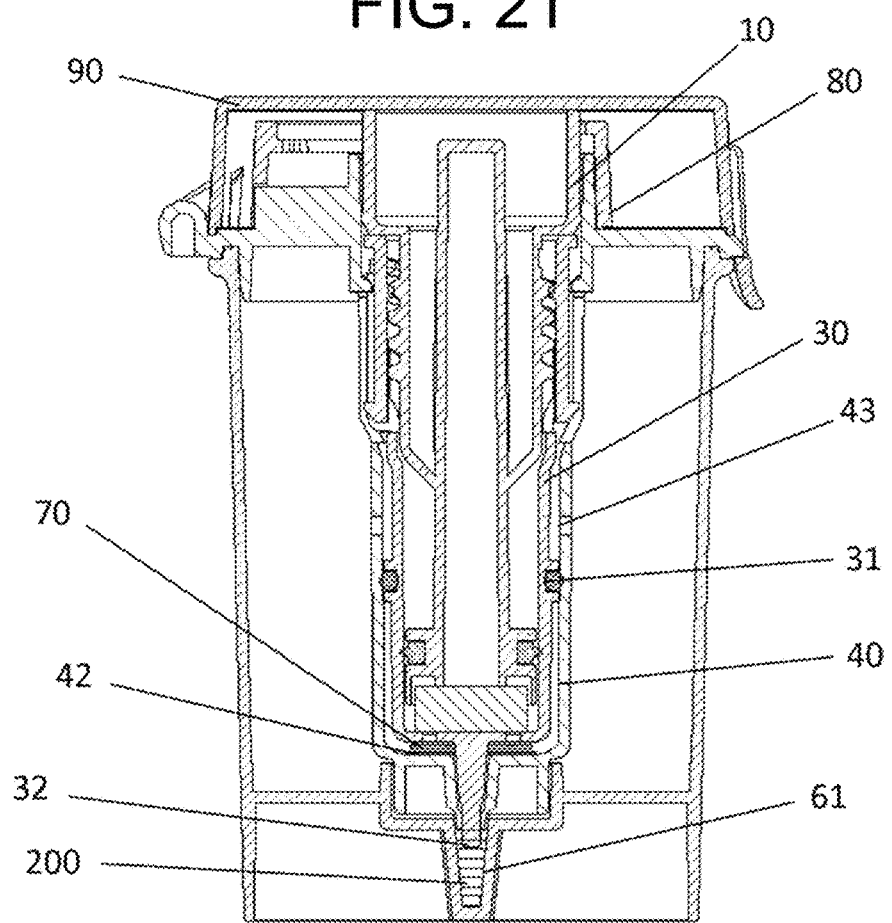
FIG. 22 is a schematic cross-sectional diagram showing that the cover is pressed on the platform of the collection outer cavity (the collection inner cavity is at a second position).

As shown in FIGS. 1-22, in the present invention, a sample collection and testing device 100 for analyzing and testing an analyte in a liquid sample includes a collection inner cavity 30 and a collection outer cavity 40. The collection inner cavity 30 is sleeved inside the collection outer cavity 40, and the collection inner cavity 30 is movable relative to the collection outer cavity 40. As shown in FIG. 14, in some embodiments, the collection outer cavity 40 includes a cavity 48 and a platform 44, and the platform 44 covers the cavity 48. During installation, the collection inner cavity 30 is first placed in the cavity 48, the platform 44 is sleeved from an upper part of the collection inner cavity 30, and a protruding point 49 inside the platform 44 is engaged with a protruding point 37 on the outer side wall of the collection inner cavity 30, so that the collection inner cavity 30 does not fall off from the collection outer cavity 40. At the same time, the collection inner cavity 30 can only move down (at the bottom portion of the collection outer cavity) along the position of the collection outer cavity 40 here. Therefore, when the protruding point 49 inside the platform is engaged with the protruding point 37 on the outer side wall of the collection inner cavity, the position of the collection inner cavity 30 in the collection outer cavity 40 is a first position, as shown in FIGS. 14, 16, 18 and 20. The position where the collection inner cavity 30 moves down to the bottom portion of the collection outer cavity 40 and stops is a second position of the collection inner cavity 30 in the collection outer cavity 40, as shown in FIG. 22. The collection inner cavity 30 communicates with the collection outer cavity 40 by means of liquid, and specifically, the two communicate with each other via through holes 36 provided at the bottom portion of the collection inner cavity 30. In a more specific embodiment, in order to quickly and thoroughly transfer the sample from the collection inner cavity 30 to the collection outer cavity 40, there may be a plurality of through holes 36 evenly distributed at the bottom portion of the collection inner cavity 30, as shown in FIG. 8. When the collection inner cavity 30 is at the first position, the collection inner cavity 30 is used to receive the collector 10 and transfer the liquid sample 200 on the collector 10 to the collection inner cavity 30, and then the liquid sample is transferred to the collection outer cavity via the through holes, as shown in FIGS. 14, 16, 18 and 20. After the collection inner cavity 30 moves to the second position at the bottom portion of the collection outer cavity 40, the liquid sample 200 in the collection outer cavity 40 is discharged out of the collection outer cavity 40, as shown in FIG. 22.

Figure 9:
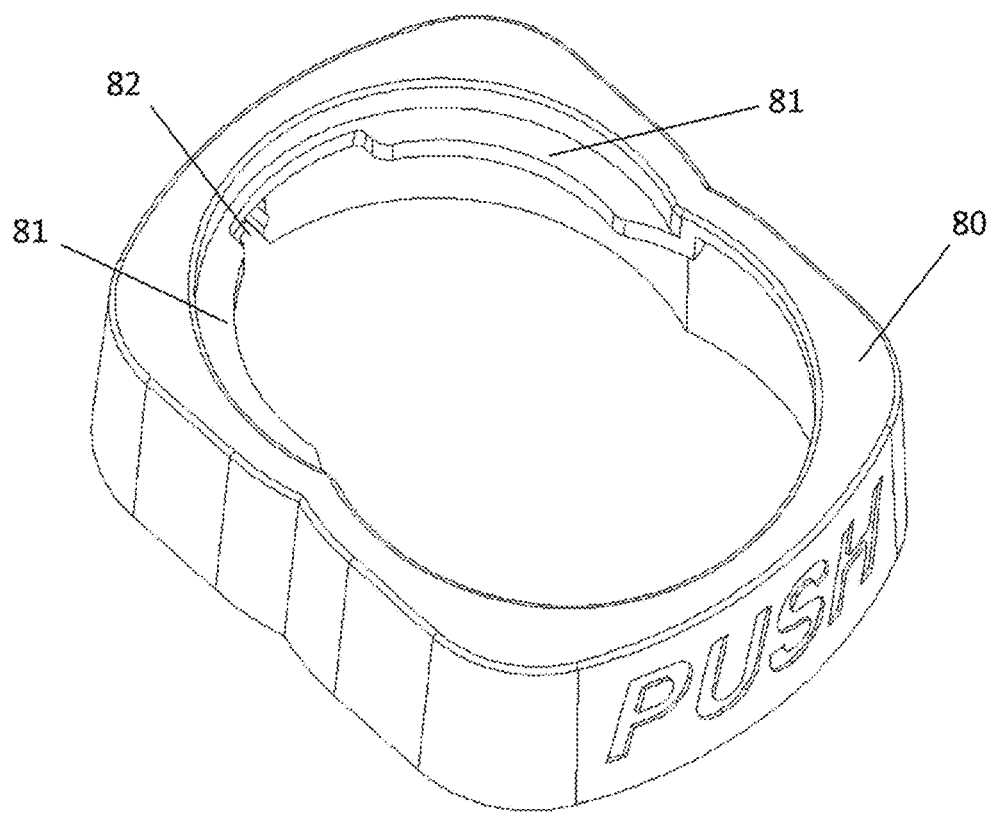
FIG. 9 is a schematic diagram of a limiting snap ring according to the present invention.
Figure 10:
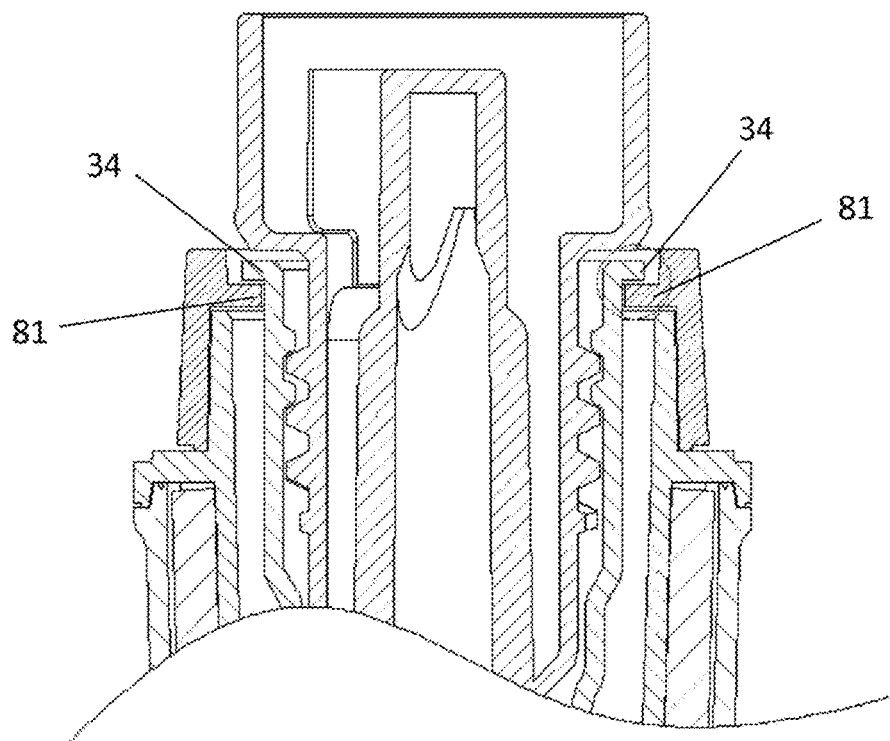
FIG. 10 is a schematic cross-sectional diagram showing that the limiting snap ring is snapped with the collection inner cavity and the collection outer cavity according to the present invention.
Figure 11:
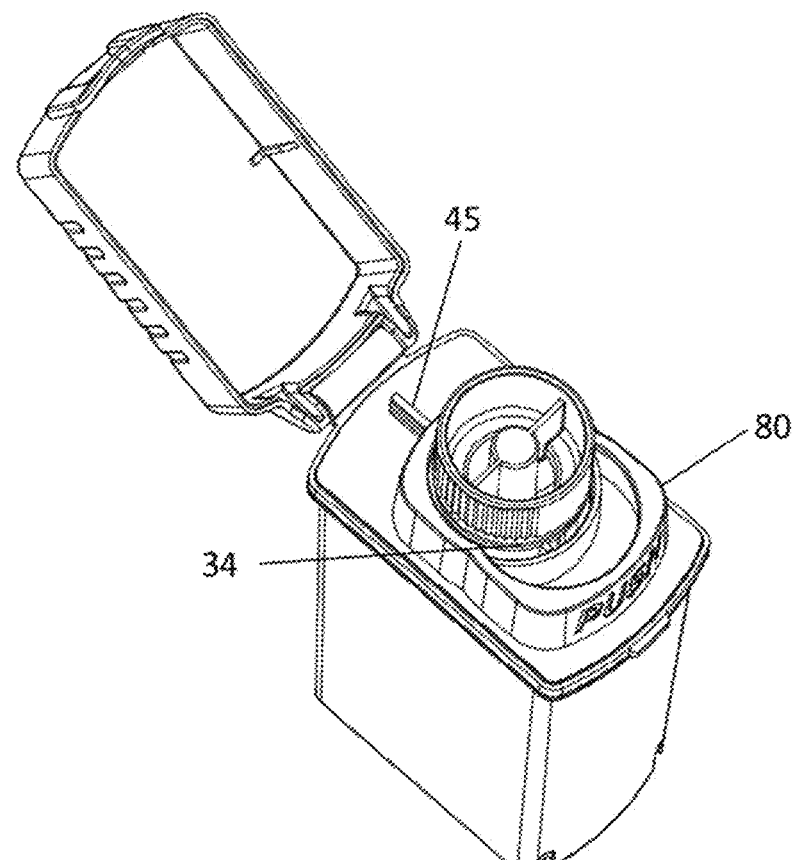
FIG. 11 is a schematic diagram showing that the limiting snap ring is snapped with the collection inner cavity and the collection outer cavity (the limiting snap ring is at a restrictive position) according to the present invention.
Figure 12:
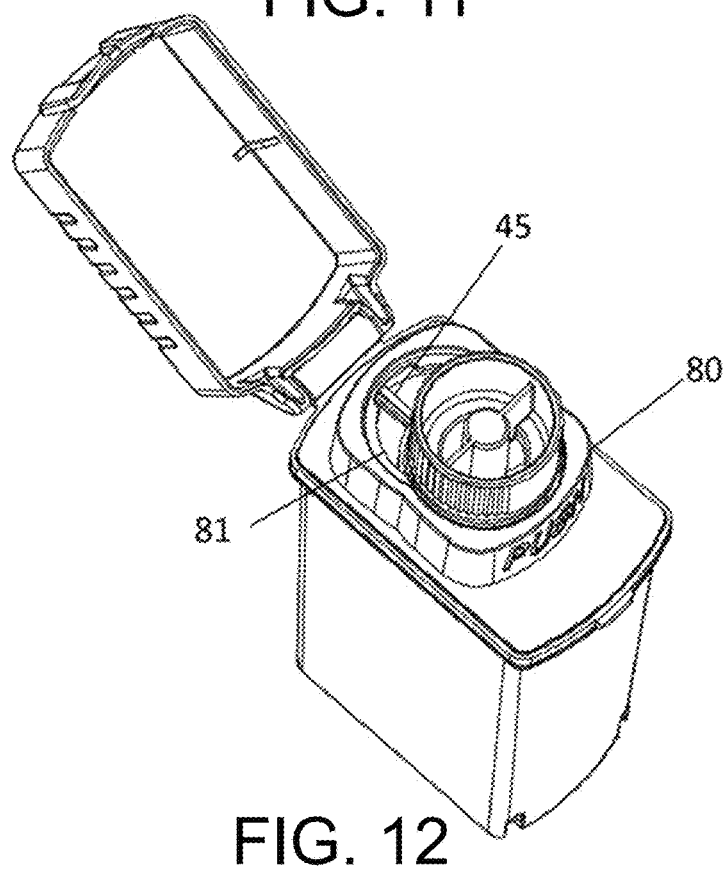
FIG. 12 is a schematic diagram showing that the limiting snap ring is not snapped with the collection inner cavity and the collection outer cavity (the limiting snap ring is at a non-restrictive position) according to the present invention.
Figure 15:
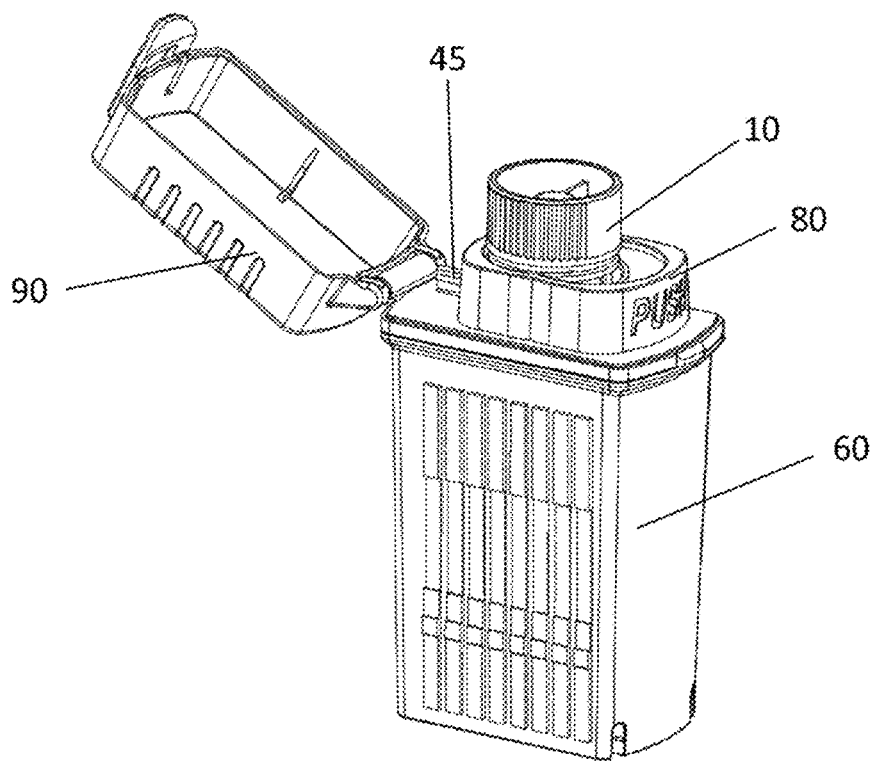
FIG. 15 is a schematic diagram showing that a collector is inserted into the collection inner cavity to collect a sample according to the present invention (the collection inner cavity is at the first position and the limiting snap ring is at the restrictive position).
Figure 17:
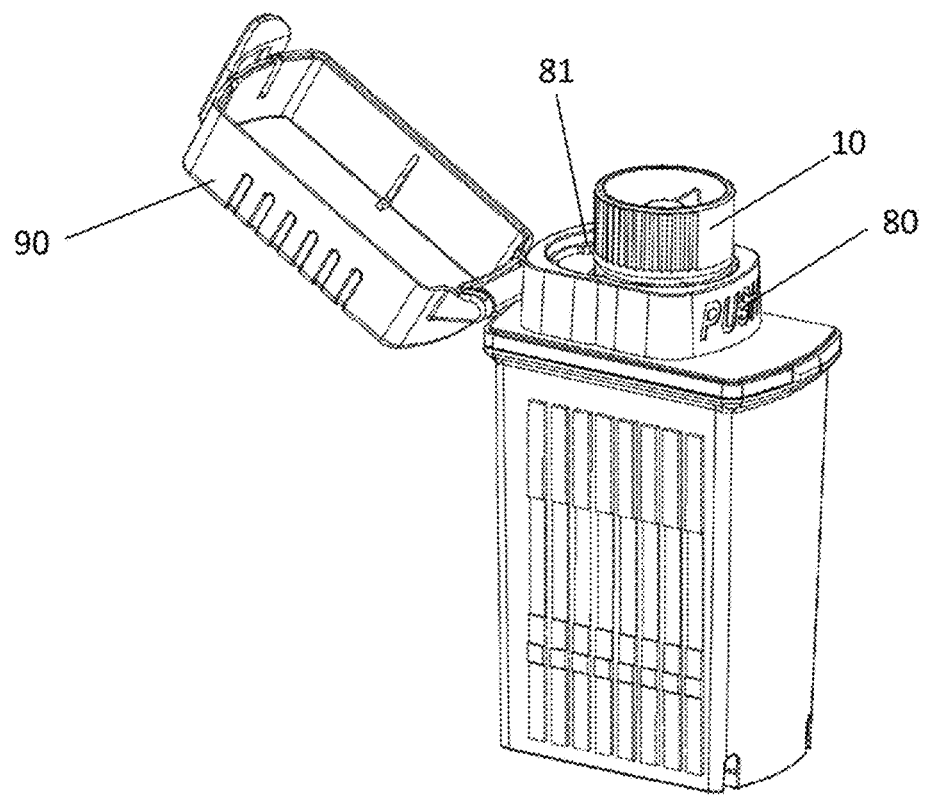
FIG. 17 is a schematic diagram showing that the limiting snap ring is at the non-restrictive position according to the present invention.

In order to control the test time of the liquid sample, or to buffer or pre-treat the sample, even if the time and operation of movement of the collection inner cavity 30 from the first position to the second position are controllable, a structure for snapping the collection inner cavity can be provided. Specifically, a limiting snap ring 80 is disposed on the collection inner cavity. By snapping or not snapping the collection inner cavity 30 with the limiting snap ring 80, the movement time of the collection inner cavity 30 in the collection outer cavity 40 is adjusted, that is, the time when the liquid in the collection outer cavity 40 is discharged. Usually, the liquid in the collection outer cavity 40 is discharged to the test cavity 20 or the test element 50 for test. Therefore, the test time becomes controllable. When the limiting snap ring 80 snaps the collection inner cavity 30, the limiting snap ring 80 is at a restrictive position on the platform 44, as shown in FIG. 11. When the limiting snap ring 80 does not snap the collection inner cavity 30, the limiting snap ring 80 is at a non-restrictive position on the platform 44, as shown in FIG. 12. In a specific embodiment, in the initial state, the limiting snap ring 80 is on the platform 44 of the collection outer cavity and snaps the collection inner cavity 30. More specifically, as shown in FIG. 9, protruding tabs 81 are provided on the inner side wall of one end of the limiting snap ring 80, and an annular outer edge 34 protruding outward is formed at the opening of the collection inner cavity 30. The tabs 81 are located under the annular outer edge 34, and snap the annular outer edge 34, as shown in FIG. 10, so that the collection inner cavity 30 is fixed on the collection outer cavity 40, and cannot move down. Generally, there are two tabs 81 symmetrically on the inner side wall of one end of the limiting snap ring 80, which is more beneficial to stably snapping the annular outer edge 34. Specifically, when the limiting snap ring 80 is at the restrictive position, the tabs 81 of the limiting snap ring are under the protruding annular outer edge 34 of the collection inner cavity, the collection inner cavity 30 is snapped onto the limiting snap ring 80, as shown in FIG. 11 and FIG. 15, and the collection inner cavity 30 cannot move in the collection outer cavity 40. When the limiting snap ring 80 is at the non-restrictive position, the tabs 81 of the limiting snap ring are far away from the protruding annular outer edge 34 of the collection inner cavity, as shown in FIG. 12 and FIG. 17, and the collection inner cavity 30 can move in the collection outer cavity 40 from the first position to the second position.

In some preferred embodiments, the limiting snap ring 80 is provided with an engaging opening 82 on a side wall between the two tabs, and the platform 44 of the collection outer cavity is provided with a strip protrusion 45. The engaging opening 82 of the limiting snap ring is sleeved on the strip protrusion 45, and the engaging opening 82 can be slid back and forth on the strip protrusion 45 so that the tabs 81 of the limiting snap ring are disposed at or away from the protruding annular outer edge 34 of the collection inner cavity. In this way, the movement trajectory of the limiting snap ring 80 is relatively fixed, which avoids the situation that the tabs do not leave the annular outer edge but continue to snap the collection inner cavity when the limiting snap ring is required not to limit the collection inner cavity, because the limiting snap ring deviates (for example, the limiting snap ring only rotates along the collection inner cavity.

Figure 16:
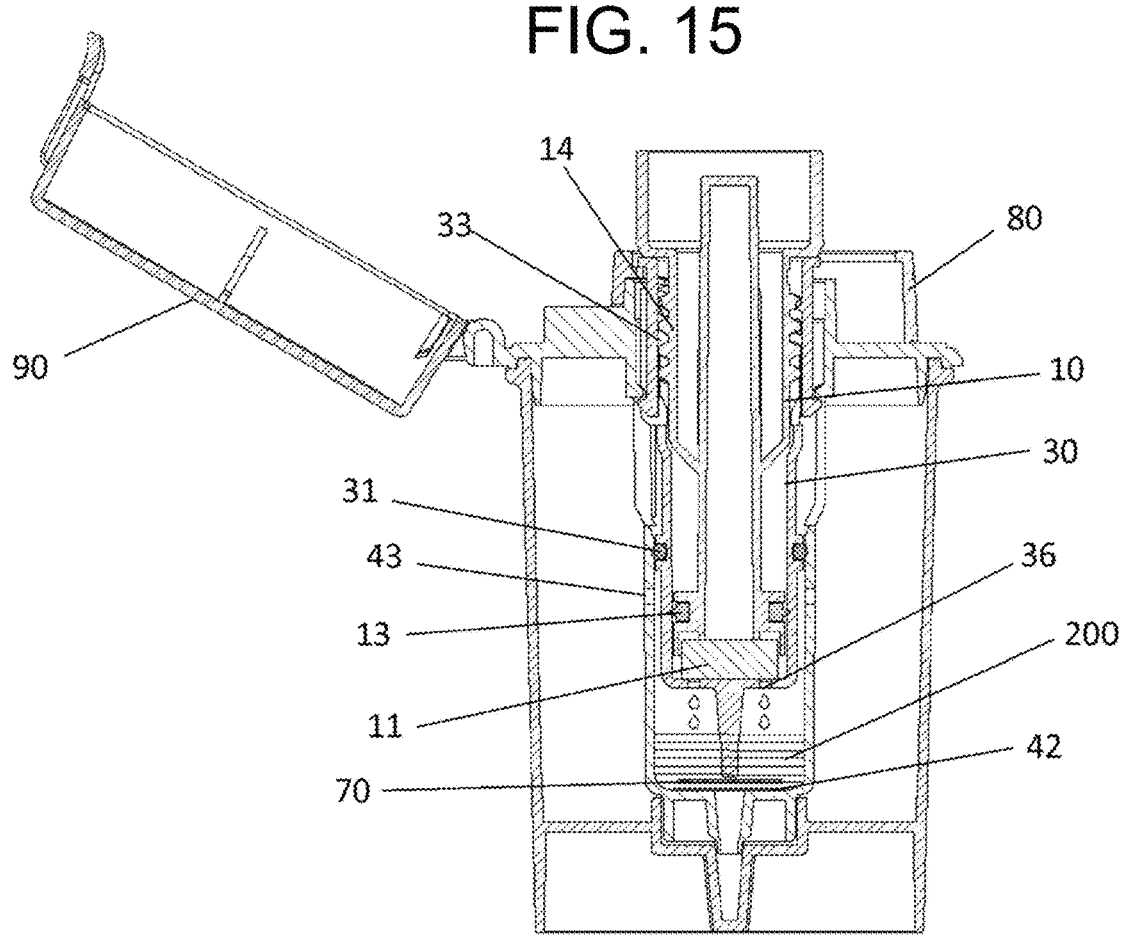
FIG. 16 is a schematic cross-sectional diagram showing that the collector is inserted into the collection inner cavity to collect a sample according to the present invention (the collection inner cavity is at the first position and the limiting snap ring is at the restrictive position).

In some embodiments, the sample needs to be buffered or pretreated, so the corresponding reagent (liquid or solid) can be added in advance to the collection outer cavity. In a preferred embodiment, the corresponding reagent can be treated on a reaction pad 70, and the reaction pad 70 is placed in the collection outer cavity 40, as shown in FIG. 14. After the liquid sample enters the collection outer cavity 40, the sample reacts with the reagent on the reaction pad 70, as shown in FIG. 16, and is thus buffered or pretreated.

In the present invention, after the absorption part 11 of the collector is inserted into the collection inner cavity 30, the absorption part 11 is fixed by screwing and squeezed by the collection inner cavity 30 to discharge the liquid sample into the collection inner cavity 30. Therefore, the upper part of the inner side wall of the collection inner cavity 30 is provided with threads 33 matching the collector. In order to squeeze and discharge the liquid sample more thoroughly, a sealing washer 13 is disposed at the collection rod 12 above the absorption part 11. The sealing washer 13 forms a seal with the side wall of the collection inner cavity 30 after entering the collection inner cavity 30, and therefore, the collection inner cavity 30 below the sealing washer 13 becomes a sealed cavity. As the collector continues to move toward the bottom portion of the collection inner cavity 30, the volume of the sealed cavity decreases, and the air pressure in the sealed cavity increases, so that the liquid is discharged more thoroughly through the through holes 36 at the bottom portion of the collection inner cavity 30. Specifically, when the collection inner cavity 30 is at the first position, the collector 10 is inserted into the collection inner cavity 30, the sealing washer 13 on the collection rod 12 is sealed with the inner side wall of the collection inner cavity 30, the absorption part 11 is squeezed after contacting the bottom portion of the collection inner cavity 30, and the liquid sample is squeezed from the absorption part 11 into the collection inner cavity 30, and then flows into the collection outer cavity 40 along the through holes 36 at the bottom portion of the collection inner cavity 30. The liquid sample flowing into the collection outer cavity 40 reacts with the reaction pad 70, and the collector 10 is fixed with the collection inner cavity 30 by screwing.

In some embodiments, the side wall of the collection outer cavity 40 is provided with an air guide hole 43. When the liquid sample in the absorption part 11 flows into the collection outer cavity 40 through the collection inner cavity 30, the air in the collection outer cavity 40 is discharged from the air guide hole 43, so that the air pressure of the collection outer cavity 40 is kept the same as the outside air pressure and is smaller than the air pressure of the sealed cavity of the collection inner cavity 30, which is more conducive to the transfer of liquid from the collection inner cavity 30 to the collection outer cavity 40.

In some embodiments, a sealing ring 31 is provided on the outer side wall of the collection inner cavity 30, and the sealing ring 31 is disposed in the middle portion of the collection inner cavity 30. More specifically, a distance between the sealing ring 31 and the bottom portion of the collection inner cavity 30 is greater than or equal to a distance between the air guide hole 43 and the bottom portion of the collection outer cavity 40. That is, when the collection inner cavity 30 is at the first position, the sealing ring 31 is above the air guide hole 43, so that the collection outer cavity 40 is in an unsealed state. The sealing ring 31 forms a seal with the inner wall of the collection outer cavity 40. When needed, the sealing ring 31 moves to the air guide hole 43 to seal the air guide hole 43.

In the present invention, an outward pointed cone protrusion 32 is provided on the outer wall of the bottom portion of the collection inner cavity 30. A channel 46 protruding outward is provided on the outer wall of the bottom portion of the collection outer cavity 40, and the bottom portion of the channel 46 is provided with an opening 47, and the channel 46 is sealed by a sealing sheet 42. When the collection inner cavity 30 moves in the collection outer cavity 40 from the first position to the second position and arrives at the second position, the pointed cone protrusion 32 of the collection inner cavity contacts and punctures the sealing sheet 42. The liquid sample in the collection outer cavity 40 flows out through the channel 46 and the opening 47. That is, when the collection inner cavity 30 is at the first position, the channel 46 is sealed by the sealing sheet 42. When the collection inner cavity 30 is at the second position, the sealing sheet 42 is punctured, and the channel 46 communicates with the outside through the opening 47. At the same time, as the collection inner cavity 30 moves from the first position to the second position and arrives at the second position, the sealing ring 31 on the outer wall of the collection inner cavity moves toward the bottom portion of the collection outer cavity 40 along the inner wall of the collection outer cavity 40, and the sealing ring 31 first seals the air guide hole 43 on the side wall of the collection outer cavity to form a sealed cavity, and then continues to move away from the air guide hole 43 to reduce the volume of the sealed cavity. In this way, the liquid 200 in the collection outer cavity 40 is discharged out of the collection outer cavity more fully and thoroughly by increasing the air pressure in the sealed cavity, thereby ensuring that the sample 200 collected on the collector 10 is discharged as much as possible for test, and ensuring the success and accuracy of the test.

The side wall on the platform 44 of the collection outer cavity is also connected to a rear cover 90. The cover 90 is movably connected to the side wall of the platform 44, and can be flipped along the platform 44 to cover the platform 44. In the present invention, in addition to the function of covering the entire device to ensure that liquid does not leak to the outside of the device to pollute the operator and the environment, the cover 90 also has the function of applying pressure to cause the collection inner cavity to descend along the collection outer cavity. Specifically, the cover 90 presses and covers the platform 44 of the collection outer cavity to press the collector 10 and the collection inner cavity 30 that are fixedly connected, so that the collection inner cavity 30 moves in the collection outer cavity 40 from the first position to the second position. After the cover 90 completely covers the platform 44, the collection inner cavity 30 is at the second position. During the process of closing the cover 90, the collector 10 and the collection inner cavity 30 are pressed down together to move down (to the bottom portion of the collection outer cavity 40), and stop moving until the cover 90 is completely fastened to the platform 40. In some embodiments, the cover 90 is provided with a U-shaped buckle 91, and the side wall of the platform 44 is provided with a protruding block 41 at the corresponding position. After the cover 90 is completely fastened to the platform 44, the U-shaped buckle 91 is at the protruding block 41 of the platform. The U-shaped buckle 91 is fastened to the protruding block 41 to lock the cover 90, the platform 44 and the outer cylinder 60, and the cover 90 continuously presses the handle 15 of the collector and the collection inner cavity 30 to ensure that the liquid in the collection outer cavity 40 continues to flow into the groove 61 of the outer cylinder.

The device 100 of the present invention further includes an outer cylinder 60 and a test element 50 in the outer cylinder. The collection outer cavity 40 is in the outer cylinder 60, and the collection outer cavity 40 communicates with the outer cylinder 60 through the channel 46 and the opening 47 at the bottom portion. More specifically, a groove 61 is provided at the bottom portion of the outer cylinder, and the bottom portion of the channel 46 and the opening 47 are in the groove 61. In this way, after the liquid sample 200 in the outer cavity 40 flows out, all the liquid sample flows into the groove 61, and the liquid sample is prevented from flowing around in the outer cylinder 60 to waste the sample.

Figure 5:
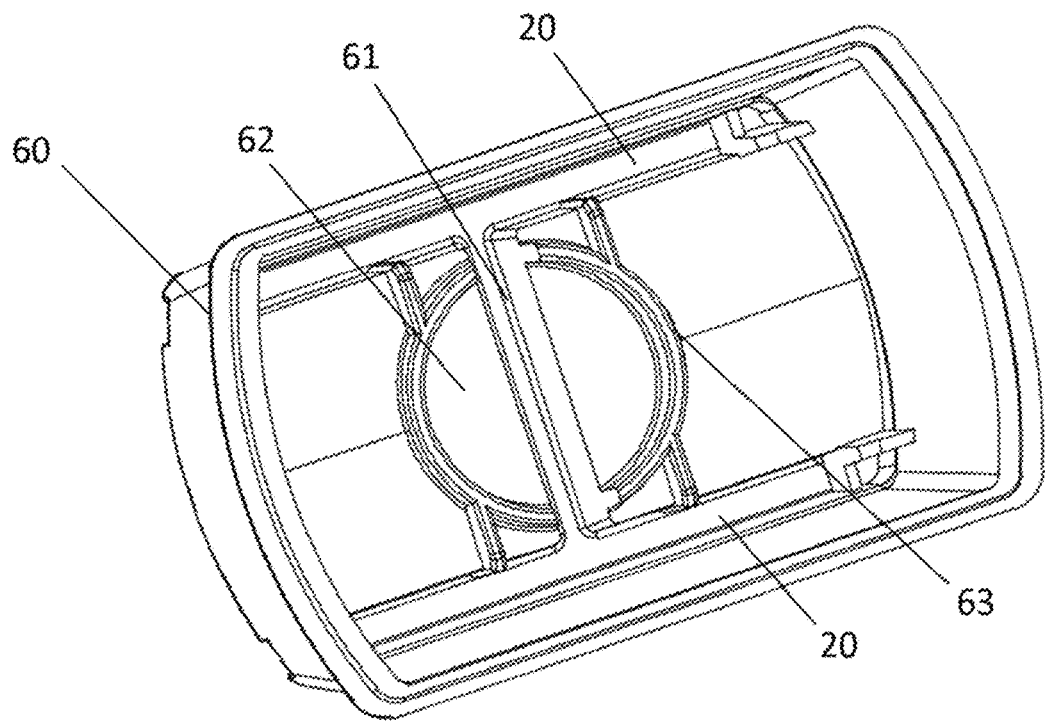
FIG. 5 is a schematic diagram of an outer cylinder according to the present invention.
Figure 6:
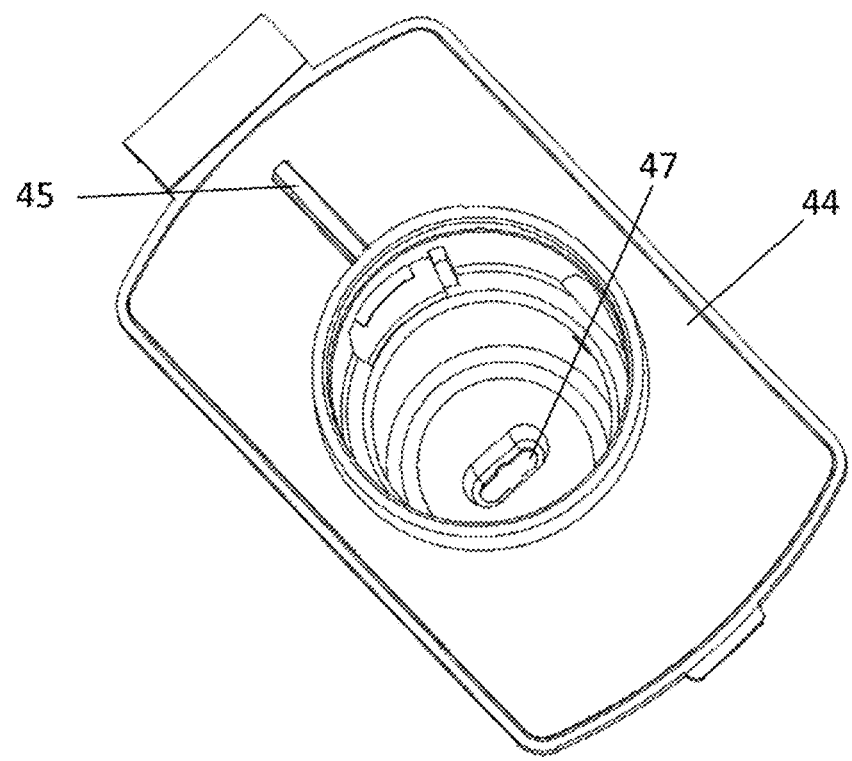
FIG. 6 is a schematic diagram of a collection outer cavity according to the present invention.
Figure 7:
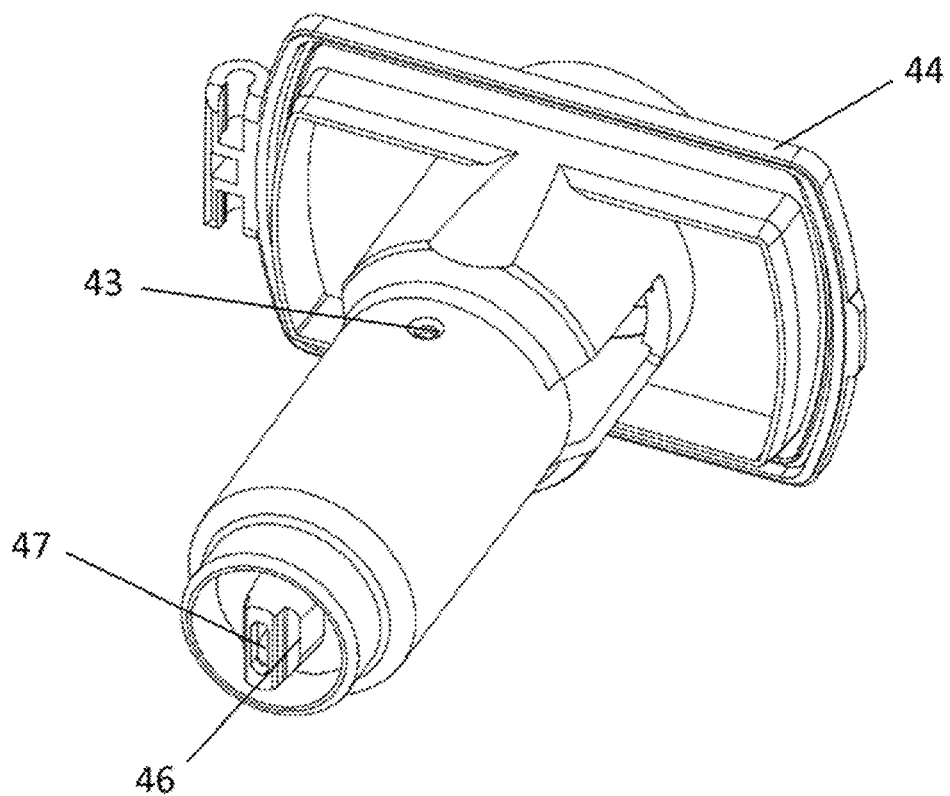
FIG. 7 is another schematic diagram of the collection outer cavity according to the present invention.

As shown in FIG. 5, in a preferred embodiment, a protruding base 62 is provided at the bottom portion of the outer cylinder 60, and a fence 63 is provided around the protruding base 62. The bottom portion of the collection outer cavity 40 is disposed on the protruding base 62, and the groove 61 is disposed on the protruding base 62.

In some embodiments, a test cavity 20 is provided at the bottom portion of the outer cylinder 60, and the test cavity 20 communicates with the groove 6. The test element 50 is disposed in the test cavity 20.

The steps of collecting and testing a sample are as follows.

Step 1. The sample collection and testing device is in the initial state, that is, the collection inner cavity is at the first position, and the limiting snap ring is at the restrictive position.

Step 2. The sample flows from the collection inner cavity into the collection outer cavity.

Step 3. The sample collection and testing device is stood for 1 to 5 minutes.

Step 4. The limiting snap ring is pushed to move from the restrictive position to the non-restrictive position.

Step 5. The collection inner cavity is moved in the collection outer cavity from the first position to the second position. At the same time, the pointed cone protrusion of the collection inner cavity contacts and punctures the sealing sheet, and the liquid in the collection outer cavity flows into the outer cylinder via the channel and the opening.

Step 6. The liquid flowing into the outer cylinder contacts the test element to complete the test.

Step 2 includes as follows.

a. The sample collector collects the liquid sample, and the absorption part is full of the liquid sample.

b. The sample collector is vertically inserted into the collection inner cavity right above the collection inner cavity, the sample collector and the collection inner cavity form a seal, the absorption part contacts the bottom portion of the collection inner cavity and is squeezed, and the liquid sample flows from the absorption part into the collection inner cavity, and then flows into the collection outer cavity via the through holes at the bottom portion of the collection inner cavity.

c. The sample collector is fixedly connected to the collection inner cavity.

The collector and the collection inner cavity move together from the first position to the second position in step 5. The sealing washer on the collection rod and a side wall of the collection inner cavity are sealed in step b to seal the sample collector and the collection inner cavity. After the liquid sample flows into the collection outer cavity in step b, the air in the collection outer cavity is discharged out from the air guide hole. When the collection inner cavity is moved from the first position to the second position in step 5, the sealing ring on the outer wall of the collection inner cavity moves toward the bottom portion of the sealed outer cavity along the inner wall of the collection outer cavity, the sealing washer first seals the air guide hole on the side wall of the collection outer cavity to form a sealed cavity, and then continues to move away from the air guide hole to reduce the volume of the sealed cavity, and the liquid in the collection outer cavity flows into the outer cylinder via the opening under the sealed air pressure. The cover is flipped and fastened onto the platform of the collection outer cavity, the fixedly connected sample collector and collection inner cavity are pressed down by the cover, and the collector and the collection inner cavity move together from the first position to the bottom portion of the collection outer cavity along the collection outer cavity until arriving at the second position.

In step 1, when the tabs of the limiting snap ring are under the protruding annular outer edge of the collection inner cavity, the collection inner cavity is snapped onto the limiting snap ring, and the limiting snap ring is at the restrictive position. In step 4, the limiting snap ring is pushed, such that the tabs of the limiting snap ring leave the protruding annular outer edge of the collection inner cavity, and the limiting snap ring is at the non-restrictive position. The liquid sample flowing into the collection outer cavity in step 2 reacts with the reaction pad in the collection outer cavity. In step c of step 2, the collector is fixedly connected to the collection inner cavity by screwing. The cover is provided with a U-shaped buckle, and the side wall of the outer cylinder is provided with a protruding block at the corresponding position. After the cover is pressed onto the platform of the collection outer cavity, the U-shaped buckle is snapped onto the protruding block to fix the cover with the outer cylinder. In some preferred embodiments, the bottom portion of the outer cylinder is provided with a groove and a test cavity communicating with the groove. The test element is in the test cavity. The bottom portion of the channel and the opening of the collection outer cavity are in the groove. In steps 5 and 6, the liquid in the collection outer cavity flows into the groove in the outer cylinder via the channel and the opening. The liquid flows from the groove to the test cavity and contacts the test element in the test cavity.

A method for collecting and testing a liquid sample by using the sample collection and testing device according to the present invention will be described in detail below.

1. The sample collection and testing device is in the initial state, that is, the collection inner cavity is at the first position, and the limiting snap ring is at the restrictive position. The protruding point of the collection inner cavity is snapped with the protruding point of the platform, the sealing sheet seals the channel of the collection outer cavity, and the tabs of the limiting snap ring are snapped under the annular outer edge of the collection inner cavity, as shown in FIGS. 13 and 14.

2. The collector collects a liquid sample and the absorption part is full of the liquid sample. Specifically, the plastic bag on the absorption part 11 is torn and removed, and the sample is collected through the absorption part 11 (for example, put into the subject's mouth to collect saliva, or put into a container that collects the liquid sample to absorb the sample), so that the absorption part 11 is full of the liquid sample.

3. The absorption part of the collector is aligned directly above the collection inner cavity, and the collector is vertically inserted into the collection inner cavity. During the movement of the collector toward the bottom portion of the collection inner cavity, the sealing washer on the collection rod seals the side wall of the collection inner cavity, the threads of the collector are screwed with the threads of the collection inner cavity, the absorption part contacts the bottom portion of the collection inner cavity and is squeezed by the bottom portion, the liquid sample on the absorption part flows out to the collection inner cavity and then flows out of the collection inner cavity via the through holes to the collection outer cavity, and the air in the collection outer cavity is discharged from the air guide hole. The collector is thoroughly screwed with the collection inner cavity and fixed, at this time, the absorption part is squeezed to a minimum state, and the liquid sample is fully discharged into the collection outer cavity, as shown in FIGS. 15 and 16.

4. The sample collection and testing device is stood for 1 to 5 minutes, and the liquid sample fully reacts with the reaction pad in the collection outer cavity.

Figure 18:
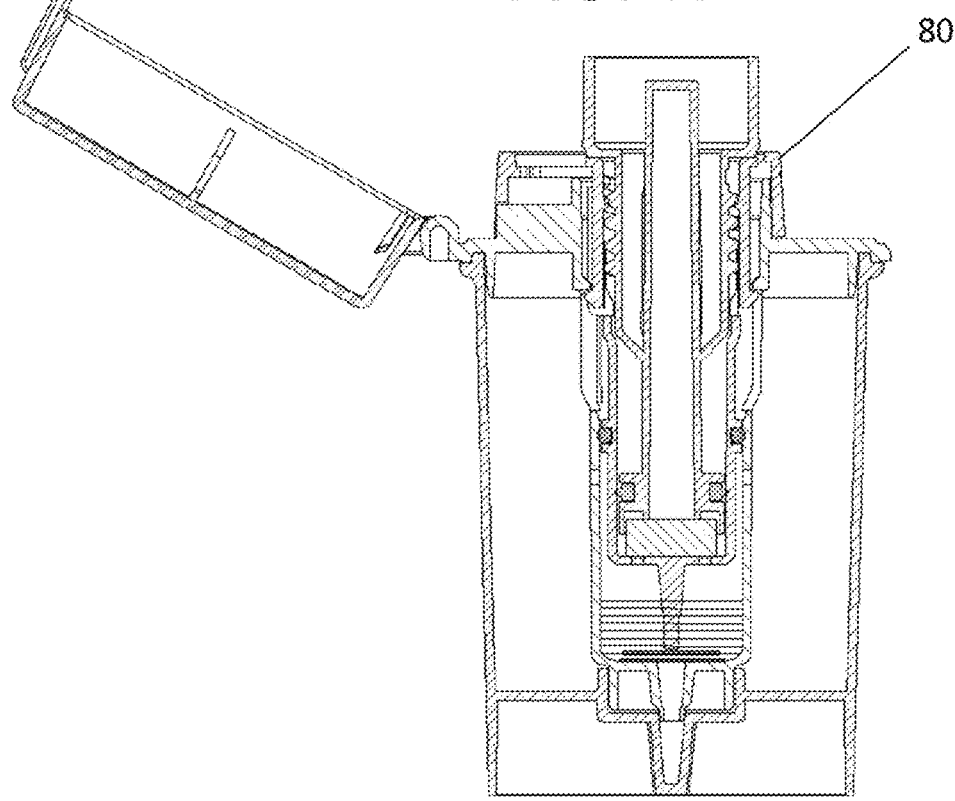
FIG. 18 is a schematic cross-sectional diagram showing that the limiting snap ring is at the non-restrictive position according to the present invention.
Figure 19:
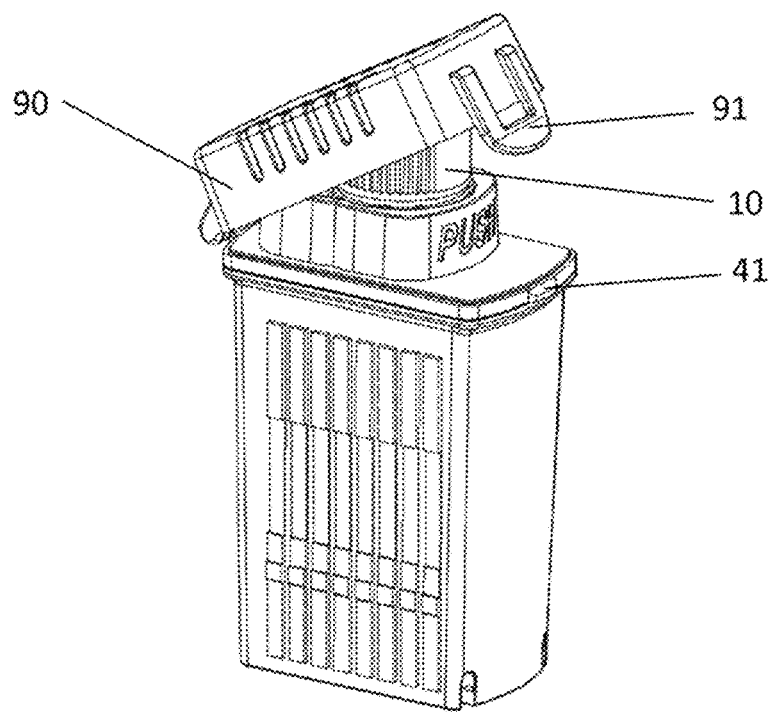
FIG. 19 is a schematic diagram showing that a cover is flipped onto a platform of the collection outer cavity.
Figure 20:
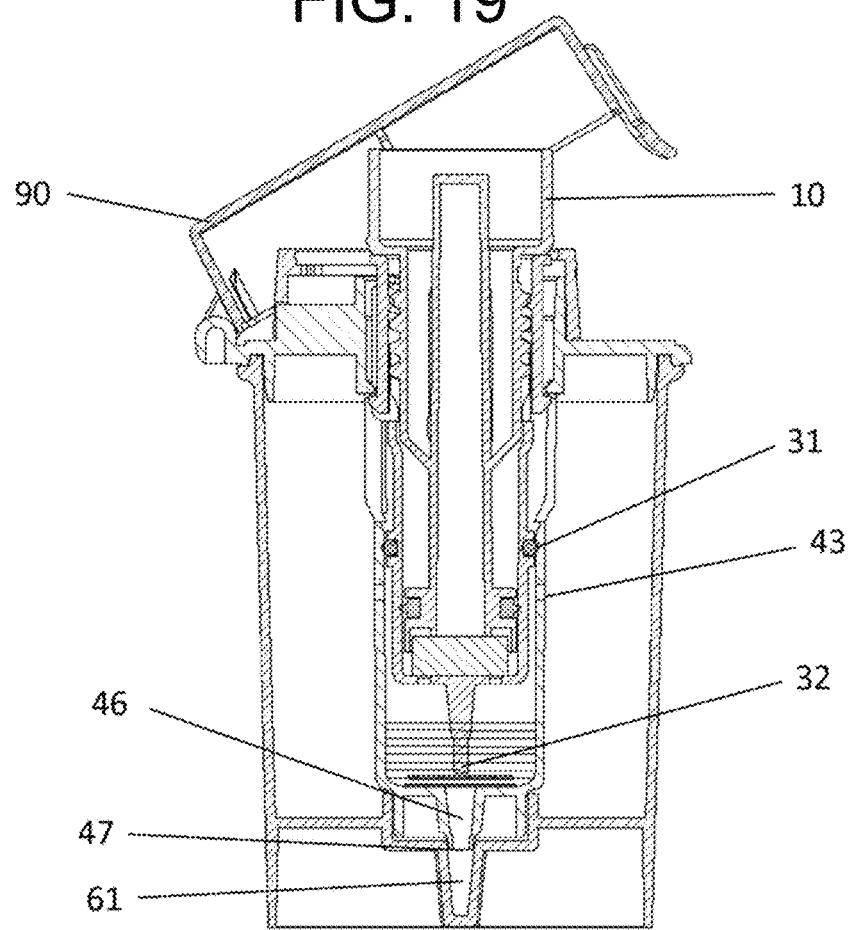
FIG. 20 is a schematic cross-sectional diagram showing that the cover is flipped onto the platform of the collection outer cavity.
Figure 21:
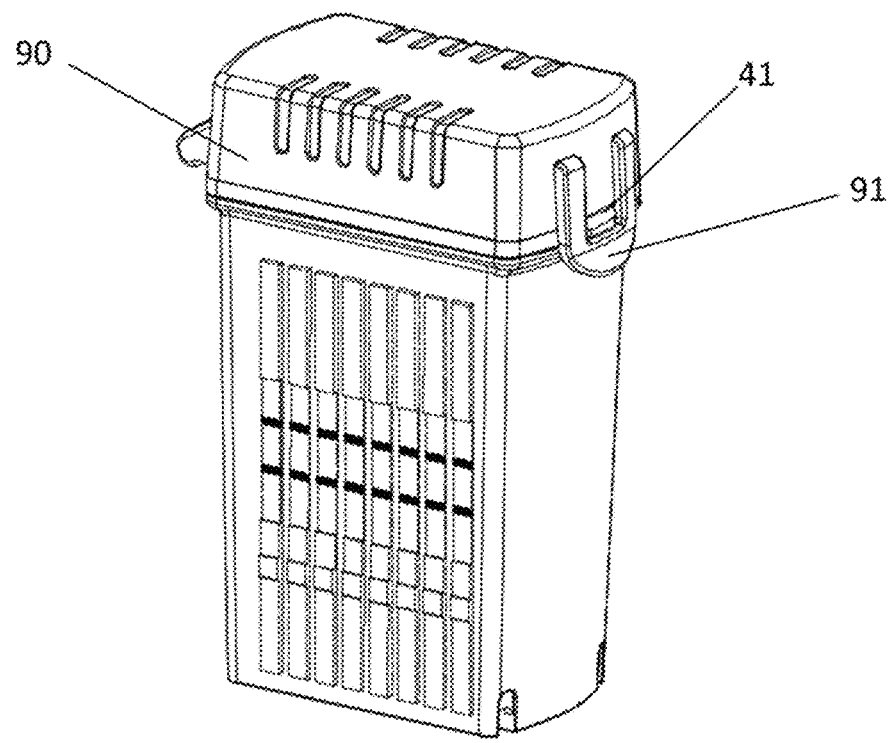
FIG. 21 is a schematic diagram showing that the cover is pressed on the platform of the collection outer cavity (the collection inner cavity is at a second position).

5. The limiting snap ring is pushed to move from the restrictive position to the non-restrictive position. The limiting snap ring moves toward the cover along the strip protrusion on the platform, and the tabs snapped under the annular outer edge of the collection inner cavity move forward and leave the annular outer edge, as shown in FIGS. 17 and 18.

6. The cover is flipped and pressed onto the platform of the collection outer cavity, the cover contacts the top handle of the collector and applies pressure to the handle, the handle and the fixedly connected collector and collection inner cavity move together from the first position to the bottom portion of the collection outer cavity along the collection outer cavity until arriving at the second position, and finally the U-shaped buckle is fastened to the protruding block of the platform. During the movement of the collection inner cavity from the first position to the second position, the sealing ring on the outer wall of the collection inner cavity moves toward the bottom portion of the sealed outer cavity along the inner wall of the collection outer cavity, and the sealing washer first seals the air guide hole on the side wall of the collection outer cavity to form a sealed cavity, and then continues to move away from the air guide hole to reduce the volume of the sealed cavity. The pointed cone protrusion of the collection inner cavity contacts and punctures the sealing sheet, and the liquid in the collection outer cavity flows into the outer cylinder through the channel and the opening under the action of the sealing air pressure, as shown in FIGS. 19-22.

7. The liquid flowing into the outer cylinder directly flows into the groove through the channel and the opening, then flows into the test cavity on the side wall of the outer cylinder through the groove, and contacts the test element to complete the test.

What is claimed is:

1. A sample collection and testing device for analyzing and testing an analyte in a liquid sample, the sample collection and testing device comprising a collection inner cavity and a collection outer cavity; wherein the collection inner cavity is disposed inside the collection outer cavity; the collection inner cavity communicates with the collection outer cavity via through holes at a bottom portion of the collection inner cavity; the collection inner cavity is movable between a first position and a second position relative to the collection outer cavity; when the collection inner cavity is at the first position, the liquid sample is collected into the collection outer cavity; and when the collection inner cavity is at the second position, the liquid sample is discharged out of the collection outer cavity, wherein the collection outer cavity comprises a cavity body and a platform at an upper part of the cavity body; the collection inner cavity is disposed inside the cavity body; a limiting snap ring is provided on the platform; the limiting snap ring has a restrictive position and a non-restrictive position on the platform; when the limiting snap ring is at the restrictive position, the limiting snap ring is snapped between the collection outer cavity and the collection inner cavity to prevent movement of the collection inner cavity in the collection outer cavity; and when the limiting snap ring is at the non-restrictive position, the limiting snap ring is not snapped between the collection outer cavity and the collection inner cavity, and the collection inner cavity is movable in the collection outer cavity from the first position to the second position.

2. The sample collection and testing device according to claim 1, wherein symmetrical tabs are provided on an inner side wall of one end of the limiting snap ring; and a protruding annular outer edge is formed at an opening of the collection inner cavity.

3. The sample collection and testing device according to claim 2, wherein when the limiting snap ring is at the restrictive position, the tabs of the limiting snap ring are under the protruding annular outer edge of the collection inner cavity, the collection inner cavity is snapped onto the limiting snap ring, and the collection inner cavity is not movable in the collection outer cavity; and when the limiting snap ring is at the non-restrictive position, the tabs of the limiting snap ring are away from the protruding annular outer edge of the collection inner cavity, and the collection inner cavity is movable in the collection outer cavity from the first position to the second position.

4. The sample collection and testing device according to claim 2, wherein the limiting snap ring is provided with an engaging opening on a side wall between the tabs.

5. The sample collection and testing device according to claim 4, wherein the platform of the collection outer cavity is provided with a strip protrusion; the engaging opening of the limiting snap ring is sleeved on the strip protrusion, and the engaging opening is slidable along the strip protrusion such that the tabs of the limiting snap ring are located at or away from the protruding annular outer edge of the collection inner cavity.

6. The sample collection and testing device according to claim 1, wherein a reaction pad is further disposed in the collection outer cavity; and when the collection inner cavity is at the first position, the liquid sample is collected into the collection outer cavity and reacts with the reaction pad.

7. The sample collection and testing device according to claim 6, further comprising a sample collector, wherein the sample collector comprises an absorption part and a collection rod, and the absorption part is connected to a bottom portion of the collection rod; and a sealing washer is disposed in a middle portion of the collection rod.

8. The sample collection and testing device according to claim 7, wherein when the collection inner cavity is at the first position, the sample collector is inserted into the collection inner cavity, the sealing washer on the collection rod is sealed with a side wall of the collection inner cavity, the absorption part is squeezed after contacting the bottom portion of the collection inner cavity, and the liquid sample is squeezed from the absorption part into the collection inner cavity, and flows into the collection outer cavity along the through holes at the bottom portion of the collection inner cavity; the liquid sample flowing into the collection outer cavity reacts with the reaction pad; and the sample collector is screwed and fixed with the collection inner cavity via external threads of the collection rod and internal threads of the collection inner cavity.

9. The sample collection and testing device according to claim 6, wherein a sealing ring is provided on an outer wall of the collection inner cavity, and the sealing ring forms a seal with an inner wall of the collection outer cavity; a side wall of the collection outer cavity is provided with an air guide hole; and after the liquid sample flows into the collection outer cavity, air in the collection outer cavity is discharged out from the air guide hole.

10. The sample collection and testing device according to claim 6, wherein an outward pointed cone protrusion is provided on an outer wall of the bottom portion of the collection inner cavity; a channel protruding outward is provided on an outer wall of a bottom portion of the collection outer cavity, and a bottom portion of the channel is provided with an opening; and the channel is sealed by a sealing sheet.

11. The sample collection and testing device according to claim 10, wherein when the collection inner cavity is at the first position, the channel is sealed by the sealing sheet; when the collection inner cavity moves from the first position to the second position and arrives at the second position, the pointed cone protrusion of the collection inner cavity contacts and punctures the sealing sheet; and the liquid sample in the collection outer cavity flows out through the channel and the opening.

12. The sample collection and testing device according to claim 9, wherein when the collection inner cavity moves from the first position to the second position and arrives at the second position, the sealing ring on the outer wall of the collection inner cavity moves toward a bottom portion of the collection outer cavity along the inner wall of the collection outer cavity, and the sealing ring first seals the air guide hole on the side wall of the collection outer cavity to form a sealed cavity, and then continues to move away from the air guide hole to reduce a volume of the sealed cavity.

13. The sample collection and testing device according to claim 10, further comprising a cover, wherein the cover is movably connected to a side wall of the platform of the collection outer cavity; the cover presses and covers the platform of the collection outer cavity to press the sample collector and the collection inner cavity that are fixedly connected, such that the collection inner cavity moves in the collection outer cavity from the first position toward the second position; and after the cover completely covers the platform, the collection inner cavity is at the second position.

14. The sample collection and testing device according to claim 11, further comprising an outer cylinder and a test element in the outer cylinder, wherein the collection outer cavity is disposed in the outer cylinder, and the collection outer cavity communicates with the outer cylinder via the channel and the opening at the bottom portion.

15. The sample collection and testing device according to claim 14, wherein a groove is provided at a bottom portion of the outer cylinder, and the bottom portion of the channel and the opening are disposed in the groove.

16. The sample collection and testing device according to claim 8, wherein an outward pointed cone protrusion is provided on an outer wall of the bottom portion of the collection inner cavity; a channel protruding outward is provided on an outer wall of a bottom portion of the collection outer cavity, and a bottom portion of the channel is provided with an opening; and the channel is sealed by a sealing sheet.

* * * * *